US009688951B2

United States Patent
Krenbrink et al.

(10) Patent No.: US 9,688,951 B2
(45) Date of Patent: Jun. 27, 2017

(54) ALGAE GROWTH SYSTEM

(75) Inventors: David Dean Krenbrink, Bridgetown (BB); Hendrik Joseph Karel Hoevers, Wageningen (NL)

(73) Assignee: ALGAE-TECH LTD., Norfolk (GB)

( * ) Notice: Subject to any disclaimer, the term of this patent is extended or adjusted under 35 U.S.C. 154(b) by 890 days.

(21) Appl. No.: 13/056,717

(22) PCT Filed: Jul. 31, 2009

(86) PCT No.: PCT/NL2009/050474
§ 371 (c)(1),
(2), (4) Date: Jul. 12, 2012

(87) PCT Pub. No.: WO2010/014010
PCT Pub. Date: Feb. 4, 2010

(65) Prior Publication Data
US 2012/0288917 A1    Nov. 15, 2012

(30) Foreign Application Priority Data
Aug. 1, 2008  (NL) ............... PCT/NL2008/050529

(51) Int. Cl.
*C12M 1/00* (2006.01)
*C12M 1/06* (2006.01)
*C12M 1/26* (2006.01)

(52) U.S. Cl.
CPC ............ *C12M 23/18* (2013.01); *C12M 21/02* (2013.01); *C12M 23/34* (2013.01); *C12M 27/06* (2013.01); *C12M 31/10* (2013.01); *C12M 33/00* (2013.01)

(58) Field of Classification Search
CPC ...... C12M 21/02; C12M 23/18; C12M 23/34; C12M 27/06; C12M 31/10; C12M 33/00
See application file for complete search history.

(56) References Cited

U.S. PATENT DOCUMENTS

| | | | | |
|---|---|---|---|---|
| 3,762,682 A | * | 10/1973 | Franck | 251/124 |
| 3,875,052 A | * | 4/1975 | Lonchamp et al. | 210/637 |
| 4,253,271 A | | 3/1981 | Raymond | |
| 4,958,460 A | | 9/1990 | Nielson et al. | |
| 5,031,990 A | * | 7/1991 | Mori | 385/25 |

(Continued)

FOREIGN PATENT DOCUMENTS

| | | |
|---|---|---|
| DE | 103 15 750 A1 | 10/2004 |
| GB | 2 425 702 A | 11/2006 |

(Continued)

OTHER PUBLICATIONS

Ugwu, C.U., Aoyagi, H., and Uchiyama, H. "Photobioreactors for mass cultivation of algae", Bioresource Technology, EPub. Mar. 2007, vol. 99, pp. 4021-4028.*

(Continued)

*Primary Examiner* — Gautam Prakash
(74) *Attorney, Agent, or Firm* — Hoffmann & Baron, LLP

(57) ABSTRACT

The invention includes a bioreactor system for growing a photosynthetic culture in an aqueous liquid and harvesting the photosynthetic culture. The present invention further relates to a method for growing a photosynthetic culture in an aqueous liquid and harvesting the photosynthetic culture. The present invention further relates to a use of a harvester system arranged to collect at least part of the scooped photosynthetic culture in a photo bioreactor system.

31 Claims, 16 Drawing Sheets

(56) References Cited

U.S. PATENT DOCUMENTS

| | | | |
|---|---|---|---|
| 5,104,803 A * | 4/1992 | Delente | 435/292.1 |
| 5,162,051 A | 11/1992 | Hoeksema | |
| 6,287,852 B1 | 9/2001 | Kondo et al. | |
| 6,602,703 B2 * | 8/2003 | Dutil | 435/292.1 |
| 7,220,018 B2 * | 5/2007 | Crabb et al. | 362/234 |
| 2008/0096267 A1 * | 4/2008 | Howard et al. | 435/257.1 |
| 2009/0148931 A1 * | 6/2009 | Wilkerson et al. | 435/286.1 |

FOREIGN PATENT DOCUMENTS

| | | | |
|---|---|---|---|
| JP | 10 098964 A | | 4/1998 |
| JP | 2006 319103 A | | 11/2006 |
| WO | 90/15953 A | | 12/1990 |
| WO | 95/19424 A1 | | 7/1995 |
| WO | 97/11154 A | | 3/1997 |
| WO | 98/24879 A | | 6/1998 |
| WO | 2005/068605 A | | 7/2005 |
| WO | 2007/087438 A2 | | 8/2007 |
| WO | 2009/066231 A2 | | 5/2009 |

OTHER PUBLICATIONS

Extracellular polysaccharide production in outdoor mass cultures of *porphyridium* sp. in flat plate glass reactors, Singh et al., Journal of Applied Phycology 12:269-275, 2000.

The Biological CO2 Fixation and Utilization Project by RITE(1, ) Usui et al., Energy Convers. Mgmt. vol. 38, Supple., pp. S487-S492, 1997.

* cited by examiner

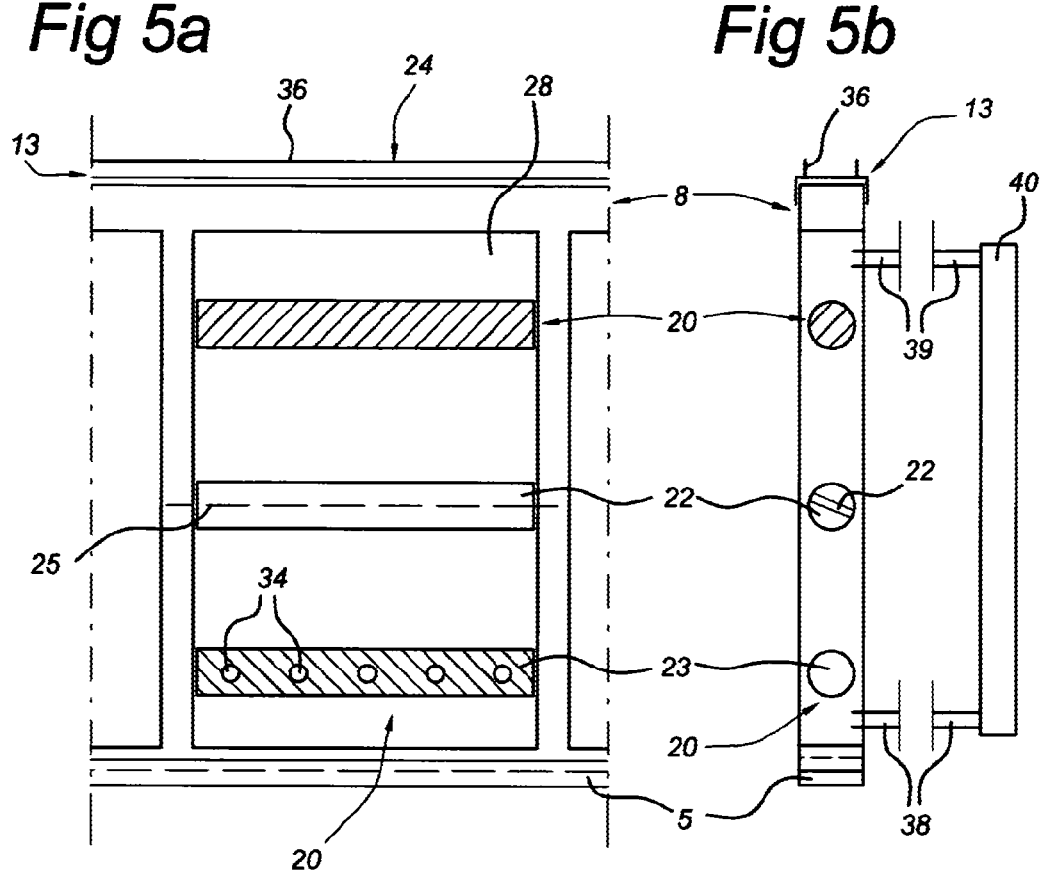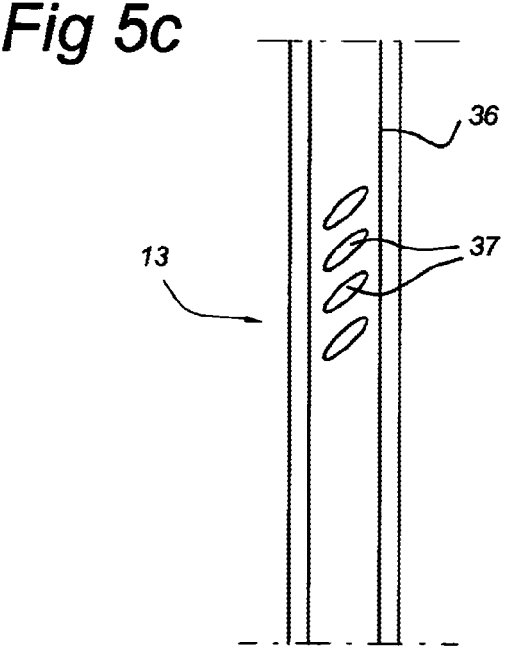

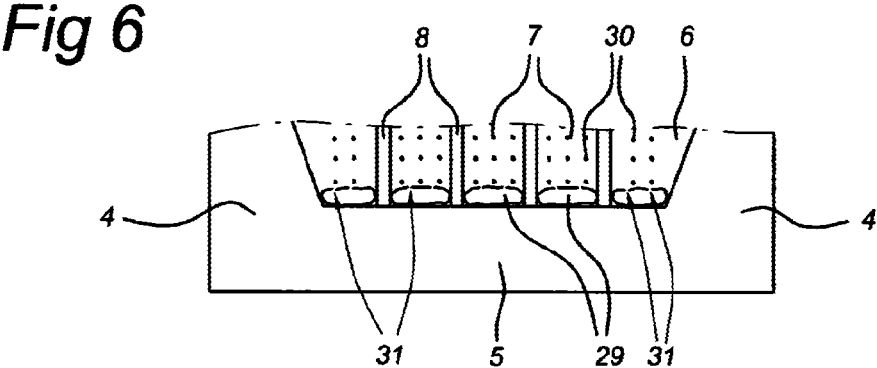
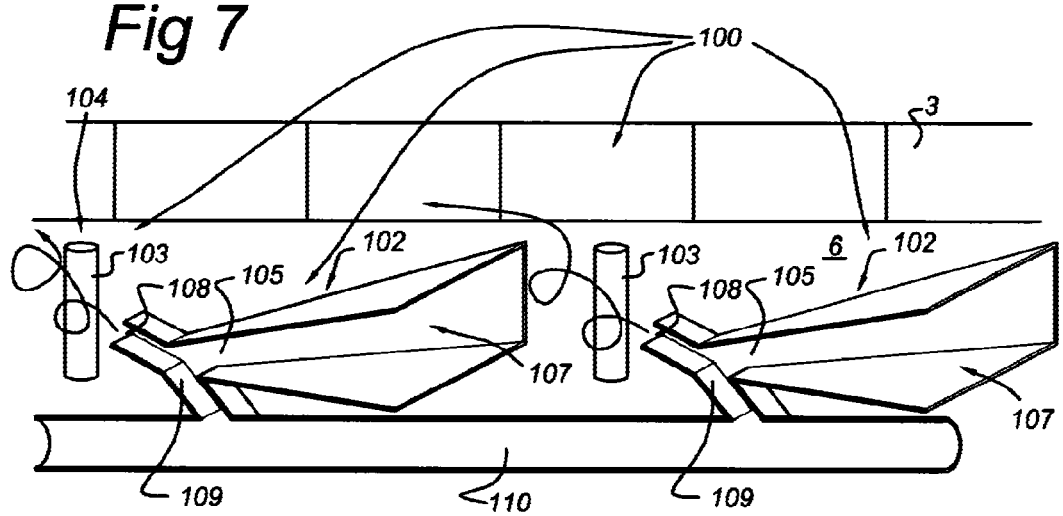
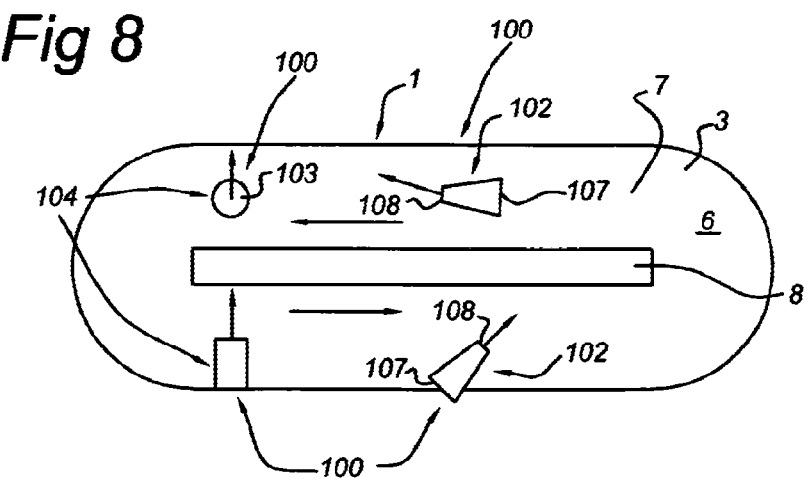

ALGAE GROWTH SYSTEM

CROSS-REFERENCE TO RELATED APPLICATIONS

This application is the National Stage of International Application No. PCT/NL2009/050474, filed Jul. 31, 2009, which claims the benefit of International Application No. PCT/NL2008/050529, filed Aug. 1, 2008, the contents of which is incorporated by reference herein.

FIELD OF THE INVENTION

The present invention relates to a bioreactor system for growing a photosynthetic culture in an aqueous liquid and harvesting the photosynthetic culture. The present invention further relates to a method for growing a photosynthetic culture in an aqueous liquid and harvesting the photosynthetic culture. In an even further aspect, the present invention relates to a lighting system for a bioreactor system and a harvesting system for a photosynthetic culture. The present invention further relates to a method for growing a photosynthetic culture in an aqueous liquid, and a method of providing lighting for the photosynthetic culture and of harvesting the photosynthetic culture.

BACKGROUND OF THE INVENTION

Algae, belonging to the class of phototrophic microorganisms, are organisms that can efficiently convert light into biomass using photosynthesis. The photosynthesis process is conversion of light energy into chemical energy by living organisms. The raw materials are carbon dioxide and water; the energy source is light; and the end-products are oxygen and (energy rich) carbohydrates.

Algae and other photosynthetic organisms have been recognized as an efficient producer of biomass, and in particular oil from which biodiesel and other fuels can be produced. During photosynthesis, algae and other photosynthetic organisms absorb carbon dioxide ($CO_2$) and light (photons) in the presence of water and produce oxygen and biomass. Dissolved nutrients may assist the process. Algae and other photosynthetic organisms can produce lipids or vegetable oils which can be harvested and converted into biodiesel and other biofuels or used directly.

The benefits of using algae to efficiently grow biomass and produce biofuel have been known for a long time, and various methods have been used to grow algae in laboratories and small scale experimental units. However, it has proven difficult to grow algae efficiently on a commercial scale.

Open pond systems have been used to grow algae on a large scale. Most of the systems used to cultivate micro-algae are shallow ponds. In these ponds, micro-algae can be cultivated with an efficiency of about 2% of sunlight in the PAR region only. PAR is the photosynthetic active region that can be used by algae and other photosynthetic organisms, i.e. sunlight with a wavelength between 400 and 700 nm. Sunlight is spread over a much broader spectrum, and the energy content of sunlight in the PAR region is only about 43% of the total energy content of sunlight. Algae can theoretically convert about 20% of the collected radiation (within PAR) into biomass. However, in most cases, this efficiency is lower because light is absorbed in a much higher rate than the rate at which photons can be converted into biomass. However, in open pond systems it is difficult to control temperature and pH, and difficult to prevent foreign algae and bacteria from invading the pond and competing with the desired algae culture. Furthermore, much of the sunlight is reflected by the water's surface, and the sunlight that does enter the pond only penetrates a small distance into the water due to the algae becoming so dense and blocking the light, so that the sunlight only reaches a thin layer of algae growing near the surface of the pond.

Bioreactors have also been used, in which nutrient-laden water is pumped through plastic or glass tubes or plates that are exposed to sunlight. Such reactors are for example known from Singh et al, Journal of Applied Phycology 12: 269-275, 2000, from Usui, Energy Conyers. Mgmt, vol. 38, Supple., pages S487-S492, 1997. The photochemical efficiency of photo bioreactor systems, especially of the flat-plate glass reactor, can reach about 16%, which is much higher than for micro-algae in ponds.

However, such bioreactors known from the state of the art have still some disadvantages. Such bioreactors are more costly and more difficult to operate than open pond systems, and they also suffer from the problem of getting the sunlight to the algae where it can be absorbed. A large portion of the sunlight is reflected from the surface of the tubes or plates. Only a small amount of the sunlight enters the water in the tubes or plates, and this small amount of sunlight only penetrates a small distance into the volume of the tube or plate. Other drawbacks of such bioreactor systems are the difficulty of temperature control, and the reliance on sunlight for growing the culture.

Algae grow best under controlled conditions. Algae is sensitive to temperature and light conditions. By controlling all aspects of the cultivation, such as temperature, $CO_2$ levels, light and nutrients, extremely high yields can be obtained.

A reactor for a photosynthetic culture is also known from Kondo et al., U.S. Pat. No. 6,287,852. A disadvantage of this reactor is the use of fixed collectors, which means that during most of the time, radiation of the sun is not collected efficiently.

WO2005068605 describes a reactor for cultivating phototrophic micro organisms, wherein the sunlight is introduced in compartment walls by using one or more moveable collimators. The compartment walls are transparent and from there light is distributed into the reactor. Such a reactor has an improved collection of radiation and an improved distribution of the radiation into the reactor, thereby providing a more efficient reactor and a more efficient cultivation of phototrophic micro organisms.

SUMMARY OF THE INVENTION

It is an aspect of the invention to provide an alternative photo bioreactor system for growing a photosynthetic culture (herein also indicated as "culture") in an aqueous liquid and harvesting the photosynthetic culture, the photo bioreactor system (herein also indicated as "bioreactor" or "reactor") comprising:

a. a vessel arranged to contain the aqueous liquid;

b. a lighting system, arranged to be at least partially submerged in the aqueous liquid, and arranged to irradiate the photosynthetic culture below the surface of the aqueous liquid;

c. a harvester system comprising a scoop construction comprising a scoop, arranged to scoop at least part of the photosynthetic culture from the aqueous liquid, and a collector system, arranged to collect at least part of the scooped photosynthetic culture.

Harvesting a part of the photosynthetic culture may set the remaining culture in a more optimal growth condition and may advantageously enable to continuously optimize the bioreactor system for growth conditions, resulting in an improved yield. An advantage of the system is that all kind of cultures may be grown and harvested.

The photosynthetic culture may be a micro-biological culture, more specifically an algae-culture for example a *spirulina* cake-culture.

The aqueous liquid may be just water, more specifically a mixture of water and nutrition (and $CO_2$) for the culture and the photosynthesis thereof.

The vessel containing the aqueous liquid may be a vessel (such as a pond). The depth of the vessel is typically from 30 cm up to significantly greater depths depending on the lighting system, such as for instance up to about 200 cm. More specifically the vessel is a series of separate vessels, more specifically a series of interconnected vessels. Hence, in a specific embodiment, the vessel comprises a plurality of vessels.

The lighting system is at least partially submerged in the aqueous liquid. Specifically the lighting system is substantially submerged in the aqueous liquid to irradiate the photo synthetic culture therein. The submerged light system may result in a better irradiation of the culture to even more improve the growth conditions for the photosynthetic culture.

It is a further aspect of the invention to provide a photo bioreactor system, wherein the photo bioreactor system is integrated in a controlled and/or closed environment, such as a greenhouse. Hence, in a specific embodiment, the invention also provides a controlled and/or closed environment, such as a greenhouse comprising the photo bioreactor system. The controlled and/or closed environment, such as a greenhouse enables one to operate the bioreactor in a controlled environment. In a specific embodiment, wherein the vessel comprises a plurality of vessels and wherein the controlled and/or closed environment, such as a greenhouse comprises a plurality of individual compartments, each individual vessel may be enclosed in its own compartment of the controlled and/or closed environment, such as a greenhouse to control the environment of each individual vessel.

It is yet another aspect of the invention to provide a photo bioreactor system wherein the scoop construction comprises a paddle wheel construction comprising at least one paddle, wherein the paddle comprises the scoop, and wherein the scoop construction is arranged to move or rotate the scoop between a position above the surface of the aqueous liquid and a position below the surface of the aqueous liquid.

In a specific embodiment the scoop construction comprises a plurality of paddle wheels, more specifically a plurality of paddle wheels arranged to rotate cw (clock wise) and another plurality of paddle wheels arranged to rotate ccw (counter clock wise), even more specifically an arrangement of plurality of paddle wheels wherein a paddle wheel is arranged to rotate cw and a neighboring paddle wheel is arranged to rotate ccw. In other words neighboring paddle wheels are arranged to rotate in opposite directions.

In a specific embodiment the paddle comprises the scoop, more specifically the paddle is substantially the scoop, and even more specifically the paddle is the scoop. In its position below the surface of the aqueous liquid the paddle wheel scoops aqueous liquid. In its position above the surface of the aqueous liquid the paddle wheel dewaters to remain the photosynthetic culture in the scoop. Within the liquid, the scoop may concentrate the culture, especially when the scoop is a sieve, arranged to sieve part of the culture from the liquid.

The photo bioreactor arrangement of the invention may advantageously allow continuous harvesting of a culture instead of batch-harvesting in known photo bioreactor systems, thereby improving the yield of the system. However, the arrangement and method of the invention may also be used for batch-harvesting. Furthermore the invention provides harvesting and swirl simultaneously in an efficient way by making use of a paddle wheel for harvesting.

It is another aspect of the invention to provide an alternative method for growing a photosynthetic culture in an aqueous liquid and harvesting the photosynthetic culture, the method comprising:

a. providing the aqueous liquid comprising the photosynthetic culture;

b. irradiate the photosynthetic culture below the surface of the aqueous liquid;

c. scooping at least part of the photosynthetic culture from the aqueous liquid, and d. collecting at least part of the scooped photosynthetic culture.

Collecting at least a part of the photosynthetic culture may set the remaining culture in the photo bioreactor in a more optimal growth condition and enables to continuously optimize the bioreactor system for growth condition resulting in an improved yield.

It is another aspect of the invention to provide a use of a harvester system comprising a scoop construction comprising a scoop, arranged to scoop at least part of the photosynthetic culture from the aqueous liquid, and a collector system, arranged to collect at least part of the scooped photosynthetic culture, in a photo bioreactor system for growing a photosynthetic culture in an aqueous liquid, for creating turbulence in the aqueous liquid and for harvesting at least part of the photosynthetic culture. Collection may done in several ways. In one embodiment, the harvester system provides the collected culture to a gutter. This gutter may be arranged on a wall of the reactor or on the panels.

The invention is also directed to the harvester system per se and to the lighting system per se.

It is another aspect of the invention to provide a flow enhancement system for a photo bioreactor system according to the invention, the flow enhancement system comprising a flow enhancement body provided with a profile for engaging the aqueous liquid for introducing turbulent flow in the aqueous liquid.

In a specific embodiment, the flow enhancement system comprises a plurality of bodies for engaging the aqueous liquid for introducing turbulent flow in the aqueous liquid. In a specific embodiment, the flow enhancement body comprises a cylinder for engaging the aqueous liquid with a cylinder wall of the cylinder.

In a specific embodiment, the flow enhancement body comprises a conduit for passing fluid from an inlet to an outlet of the conduit; in a more specific embodiment the profile comprises an fluid inlet coupled with the conduit for passing the aqueous liquid through the conduit. Alternatively, the inlet may be coupled (i.e. in liquid contact) with a supply conduit for supplying one or more of fresh water, nutrients and the like, to the aqueous liquid. In an even more specific embodiment, the flow enhancement body comprises a further inlet for fluid coupling the conduit to the supply conduit. In a specific embodiment the outlet is arranged to direct the fluid towards a neighboring flow enhancement body. In a specific embodiment the outlet is arranged to direct the fluid upwards.

It is another aspect of the invention to provide a photo bioreactor system comprising a flow enhancement system according to the invention.

The invention is also directed to the flow enhancement system per se.

It is another aspect of the invention to provide a lighting panel for a lighting system of a photo bioreactor system, such as for instance described herein, the lighting panel comprising transparent sidewalls forming a compartment, a light source provided in the compartment for lighting the algae, coupling means for accommodating the lighting panel in a wall comprising coupled light panels. The wall comprising coupled light panels is suitable for forming canal sections, also known as raceways, in a vessel of the photo bio reactor system. The lighting panel may comprise transparent sidewall, as mentioned above. However, the panels may also comprise walls, wherein light sources are integrated and/or attached to. In this way, light may be supplied from the walls to the liquid.

In a specific embodiment the compartment comprises a plurality of light sources, more specifically each of these lights sources are arranged to provide light with a specific wavelength, e.g. between 400-450 nm and/or 640-680 nm, even more specifically the light source or sources comprises a light emitting diode.

It is another aspect of the invention to provide a photo bioreactor system comprising a light panel according to the invention, specifically coupled light panels forming a wall.

In a specific embodiment of the wall, the wall comprises a frame for coupling and supporting the light panels.

In yet another embodiment, the invention provides a photo bioreactor system for growing a photo synthetic culture in an aqueous liquid, the photo bioreactor system comprising:
  a. a vessel arranged to contain the aqueous liquid;
  b. a lighting system, arranged to be at least partially submerged in the aqueous liquid, and arranged to irradiate the photosynthetic culture below the surface of the aqueous liquid;
  c. a paddle wheel construction, arranged to create turbulence in the liquid.

In this way, turbulence, and especially flow, may be created in the bioreactor. Such reactor may further comprise one or more flow enhancement systems as described herein. Harvesting may be performed with methods known in the art, but may also be performed with the paddle wheel construction and a collector system.

In yet another embodiment, the invention provides a method for growing a photosynthetic culture in an aqueous liquid and harvesting the photosynthetic culture, the method comprising:
  a. providing the aqueous liquid comprising the photosynthetic culture;
  b. irradiate the photosynthetic culture below the surface of the aqueous liquid;
  c. creating turbulence, especially a flow, in the aqueous liquid;
  d. removing at least part of the photosynthetic culture from the aqueous liquid, and
  e. collecting at least part of the removed photosynthetic culture.

The removal of the culture may especially be done with the harvesting system as described herein, but may also be performed with method known in the art. The turbulence is especially created with the paddle wheel construction as described herein. In an embodiment, the harvesting system is used to create turbulence in the liquid and to remove (scoop) culture from the liquid. Flow may alternatively or additionally also be created by injection in the liquid of water and/or nutrients. In a specific embodiment, turbulence is (also) created by providing water and/or nutrients to the liquid with a turbulence enhancement system, especially funnel type of the turbulence enhancement system.

The invention also relates to a method for growing a photosynthetic culture in an aqueous liquid and harvesting the photosynthetic culture, the method comprising:
  a. providing the aqueous liquid comprising the photosynthetic culture;
  b. irradiate the photosynthetic culture below the surface of the aqueous liquid wherein the photosynthetic culture is irradiate from a wall of a reactor containing the photosynthetic culture and optionally also from an obstacle, arranged in the reactor and arranged in the liquid, wherein the obstacle is a cylindrical obstacle (and wherein the obstacle is not arranged as wall).

As a further example, the type of lighting emanating from the wall is another type of lighting than light emanating from the obstacle. E.g., the blue content of the light from the obstacle is larger than the blue content of the light from the wall. Especially, the wall comprises light source(s) generating blue and red light, whereas the obstacle(s) may comprise light source(s) generating blue light.

The various aspects discussed in this patent can be combined in order to provide additional advantageous advantages.

The present invention in a further aspect aims to provide an improved bioreactor using LED lighting system to at least partially provide the light for the algae.

For this purpose, embodiments of the invention relate to a lighting system for illuminating a photosynthetic culture in an aqueous liquid comprising a light source comprising a plurality of LEDs, a mounting structure for supporting the LEDs, and a housing for accommodating the light source and the mounting structure, at least a portion of the housing being transparent for light emitted by the light source, wherein the housing is at least partly filled with a cooling liquid, such that, in use, heat from the LEDs is transferred by the cooling liquid from the LEDs by means of convection.

In embodiments, the invention relates to a reactor for growing a photosynthetic culture in an aqueous liquid, the reactor comprising a tank for accommodating the aqueous liquid with the photosynthetic culture in it; and abovementioned lighting system for illumination of the photosynthetic culture, wherein the lighting system is at least partially submerged in the aqueous liquid.

In embodiments, the invention relates to a reactor for growing a photosynthetic culture in an aqueous liquid, the reactor comprising: a tank for accommodating the aqueous liquid with the photosynthetic culture in it; and a lighting system comprising a light source comprising a plurality of LEDs, a mounting structure for supporting the LEDs, and a housing for accommodating the light source and the mounting structure, at least a portion of the housing being transparent for light emitted by the light source; wherein substantially all of the transparent portion of the housing is submerged in the aqueous liquid so that substantially all of the light emitted from the lighting system enters the aqueous liquid below the top surface of the aqueous liquid.

In embodiments, the invention relates to a method for growing a photosynthetic culture in an aqueous liquid, the method comprising: providing an aqueous liquid with the photosynthetic culture in it, providing a lighting system at least partially submerged in the aqueous liquid, the lighting system comprising a plurality of LEDs, providing a cooling liquid for cooling the LEDs of the lighting system, and irradiating the photosynthetic culture with light generated by the LEDs, the light being transmitted through the cooling liquid and into the aqueous liquid in a region below the top surface of the aqueous liquid.

In embodiments, the invention relates to a method for transferring light generated by a light emitting diode towards an aqueous liquid containing a photosynthetic culture, the method comprising: emitting light by the light emitting diode, the light emitting diode having a first refractive index; transferring the light through a liquid medium having a second refractive index; further transferring the light through a solid medium having a third refractive index; and passing the light into the aqueous liquid, the aqueous liquid having a fourth refractive index; wherein the values of the first, second, third and fourth refractive index form a sequence with a descending order.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 5A schematically depicts in side view an embodiment of a lighting panel comprised in the bioreactor system according to the invention;

FIG. 5B schematically depicts a cross section of the lighting panel of FIG. 5A;

FIG. 5C schematically depicts a top view of the lighting panel of FIG. 5A.

FIG. 6 schematically depicts in cross section a detail of an embodiment of a vessel comprising a $CO_2$-applicator;

FIG. 7 schematically depicts in perspective view a flow enhancement system;

FIG. 8 schematically depicts in top view a flow enhancement system;

DETAILED DESCRIPTION OF EMBODIMENTS

Figure 1:
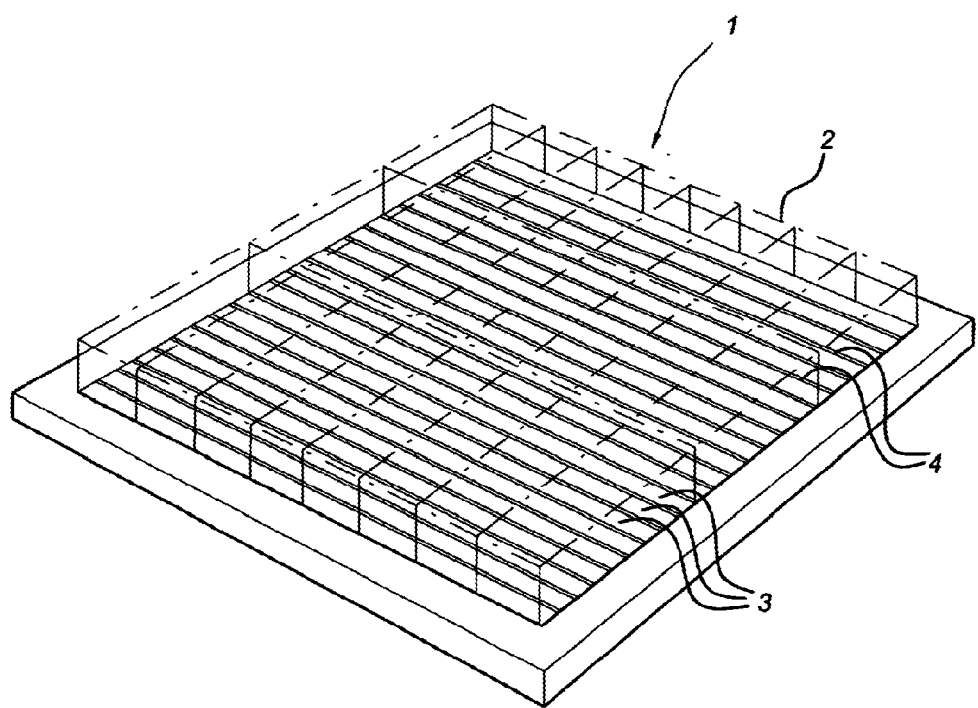
FIG. 1 schematically depicts, in perspective view, a bioreactor system according to the invention.

The following is a description of various embodiments of the invention, given by way of example only and with reference to the drawings. In a specific embodiment of the photo bioreactor system according to the invention, the lighting system comprises a light source arranged to irradiate the photosynthetic culture below the surface of the aqueous liquid. This may mean that the light source is arranged to be situated below the surface of the liquid during use of the photo bioreactor system. In a more specific embodiment the light source is at least partly submerged in the aqueous liquid below the surface of the aqueous liquid. In an even more specific embodiment the light source is submerged in the aqueous liquid. In an embodiment the light source emits substantially light in the photosynthetically active radiation (par) spectrum and may be selected from one or more of the group consisting of incandescent lamps, LEDs (solid state LEDs or OLEDs), fluorescent lamps, gas discharge lamps, cold cathode lamps, etc. Especially LEDs may be used.

Especially, the light source is arranged to substantially emit light having a wavelength selected from the range of about 600-730 nm, such as 620-665 nm, and especially in the range of 640-680 nm. In another embodiment, the light source is arranged to provide light in the range of 400-500 nm, especially 400-450 nm. Especially, both types of light, red and blue, is provided. This may especially enhance the photosynthetic efficiency (and consequently energy efficiency as well).

In a specific embodiment of the photo bioreactor system according to the invention, the lighting system comprises a reflector arranged to reflect light of the light source below the surface of the aqueous liquid into the aqueous liquid. This may mean that that the reflector is arranged to be situated below the surface of the liquid during use of the photo bioreactor system. In this way, light of the light source may be at least partially reflected into the liquid. In a more specific embodiment one or more reflectors are arranged below one or more light sources (respectively) and are arranged to direct at least part of the light to the aqueous liquid (especially below the light source). In this way, light may penetrate deeper into the liquid. In an even more specific embodiment the reflector is arranged to rotate during use of the photo bioreactor system to "scatter" the light through the aqueous liquid so as to enhance grow condition for the photosynthetic culture. The reflector may be arranged to reflect specular or to reflect diffusive.

In a specific embodiment of the photo bioreactor system, the scoop comprises a sieve, arranged to scoop a predetermined fraction of the photosynthetic culture. In a specific embodiment the scooped (harvested) fraction is between 10-60 wt. % of the culture/day, depending on the growth rate of the photosynthetic culture.

The photo bioreactor system may advantageously allow continuous harvesting. Continuous harvesting is advantageous over known batch-harvesting of a complete vessel. It enables one to keep a vessel in optimal culture grow conditions and enhances overall yield of the bioreactor system. The photosynthetic culture may comprise micro algae, but also other species that can convert radiation (of the sun) into biomass like for example photosynthetic purper bacteria. In this invention, the photosynthetic culture may comprise at least one or more of the group consisting of the cyanobacteria, the Rhodophyta (red algae), the Chlorophyta (green algae), Dinophyta, Chrysophyta (golden-brown algae), Prymnesiophyta (haptophyta), Bacillariophyta (diatoms), Xanthophyta, Eustigatophya, Rhaphidophyta, Phaeophyta (brown algae) and photosynthetic purper bacteria. Also *Botryococcus* may be applied; especially such species are applied because of the accessibility of oil. However, photosynthetic culture (sometimes also indicated as phototropic micro organisms) according to this invention may also comprise cell cultures of other organisms like e.g. micro algae, genetically modified micro algae, genetically improved micro algae, etc.

In a specific embodiment of the photo bioreactor system, the scoop comprises meshes, and the meshes in an embodiment have a mesh size in the range of about 0.5-10 µm, such as 0.5-20 µm, like especially 0.5-10 µm, to scoop a fraction of the photosynthetic culture with a predetermined size, e.g. mature algae. In a more specific embodiment the mesh size is adjustable for example by adjusting a scoop itself or by exchanging scoops with different meshes.

In a specific embodiment of the photo bioreactor system, the harvester system further comprises a harvester transporter, arranged to allow the scoop construction scoop at different positions in the aqueous liquid. In a more specific embodiment the transporter comprises a rail. It is advantageous to harvest the culture evenly over all the aqueous liquid.

In a specific embodiment of the photo bioreactor system, the collector system further comprises a product transporter, arranged to transport the collected scooped photosynthetic culture to a storage unit.

In a specific embodiment of the photo bioreactor system, the photo bioreactor system further comprises a dryer, arranged to dry the collected scooped photosynthetic culture.

In a specific embodiment of the photo bioreactor system, the scoop construction comprises the paddle wheel construction, and the collector system is arranged to receive the scooped photosynthetic culture dropping from the scoop. The scoop dewaters the culture when it is out of its position below the surface of the aqueous liquid. The remaining dewatered culture is dropped in the collector system while the scoop is in its second position above the surface of the aqueous liquid, more specifically while the scoop is in its dropping position, that means while the scoop is above the collector system at an appropriate inclination so that the scooped photosynthetic culture can drop in/on the collector system, more especially a receiver, such as a container, from the collector system.

In a specific embodiment of the photo bioreactor system, the harvester system is further arranged to create turbulence in the aqueous liquid, specifically the scoop construction is arranged to create turbulence, more specifically the scoop is arranged to create turbulence in the aqueous liquid. Compared with a laminar flow, the turbulent flow creates far better growth conditions for the culture.

In a specific embodiment a $CO_2$-applicator is arranged to contribute as well to turbulence in the aqueous liquid.

The purpose of the $CO_2$-applicator is to provide $CO_2$ to the aqueous liquid.

More specifically, different applicators can be located along the length of the raceway to provide $CO_2$. The $CO_2$ is applied in such a way, that is the amount and the rate of addition, and in such a form (liquid or gaseous) that the optimal growth conditions are maintained in the raceway, in time and at all locations in the raceway. It is possible to combine the addition of the $CO_2$ with the addition of other components (fresh water, nutrients, salts). Controlling the addition of the $CO_2$ has two main purposes.

First, the $CO_2$ is added in such a way (amount, rate, form, location) with the purpose to control the pH of the liquid. More specifically, the addition of the $CO_2$ is in such a way that the optimal pH will be maintained. The $CO_2$ is added in such a way that the pH is between 8 and 12.

Second, the $CO_2$ is added in such a way (amount, rate, form, location) that the optimal concentration of the different species ($CO_2$, nutrients, salts) in the aqueous liquid is assured. The optimal concentration will assure for an optimal uptake (amount and rate) of the $CO_2$ and the nutrients by the micro-algae.

To enable the maintaining the optimal pH levels for the various algae species it grows it is desired to be able to meet the increased demand for $CO_2$ in its algae growing system. Hence, nutrients particularly from effluents such as farms and waste water with $CO_2$ which in a liquid, dry or foam state that can absorb 10-20 times more $CO_2$ than water, or $CO_2$ direct from the air. Further, by adding the $CO_2$ to the growing medium in a liquid, dry or foam it is possible to deliver the $CO_2$ into the system without bubbles which cause shear stress and can damage the algae.

Nutrients, especially liquid nutrients, contain nitrates amongst others, may absorb a much higher concentration of $CO_2$ than for instance ("pure") water, this may enable to increase a higher absorption concentration, and keep them liquid for faster and easier uptake by the algae with minimal or no shear stress which may normally caused by (too much) bubbles.

FIG. 1 schematically depicts a photo bioreactor system 1 (herein also indicated as "photo bioreactor" or "bioreactor") to grow aqueous micro organisms, in particular a photosynthetic bio-culture, in particular algae, at a large scale. The bioreactor system 1 may easily extend over several hectares up to even hundreds of hectares. In this embodiment the bioreactor system 1 comprises a plurality of vessels 3 wherein the algae are grown. The individual vessels 3 are separated by vessel walls 4. The vessels 3 have a depth a, as indicated in FIG. 2B, in the range of 30 cm up to several meters. The vessels 3 are enclosed by a controlled and/or closed environment, such as a greenhouse 2 to provide a controlled environment to grow algae, possibly a controlled environment is provided for every individual vessel 3.

Figure 2A:
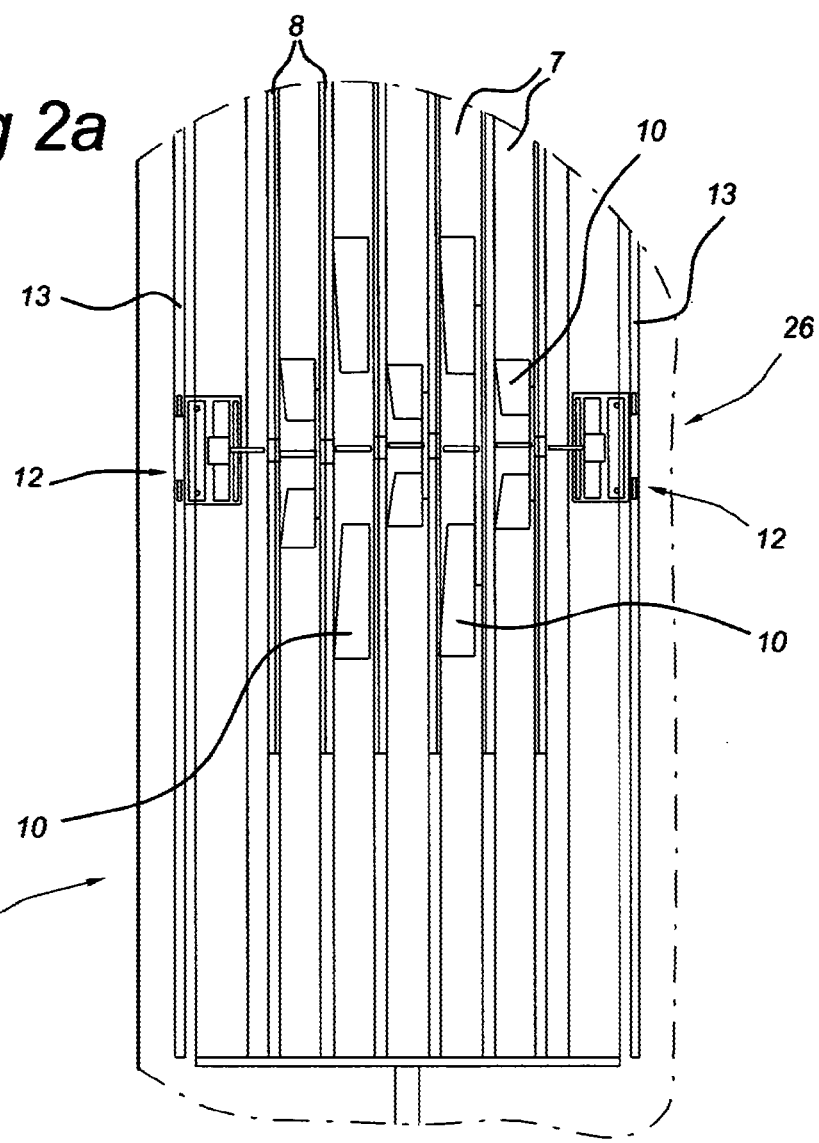
FIG. 2A schematically depicts in top view, a detail of an embodiment of a vessel and a harvester system comprised in the bioreactor system according to the invention.
Figure 2B:
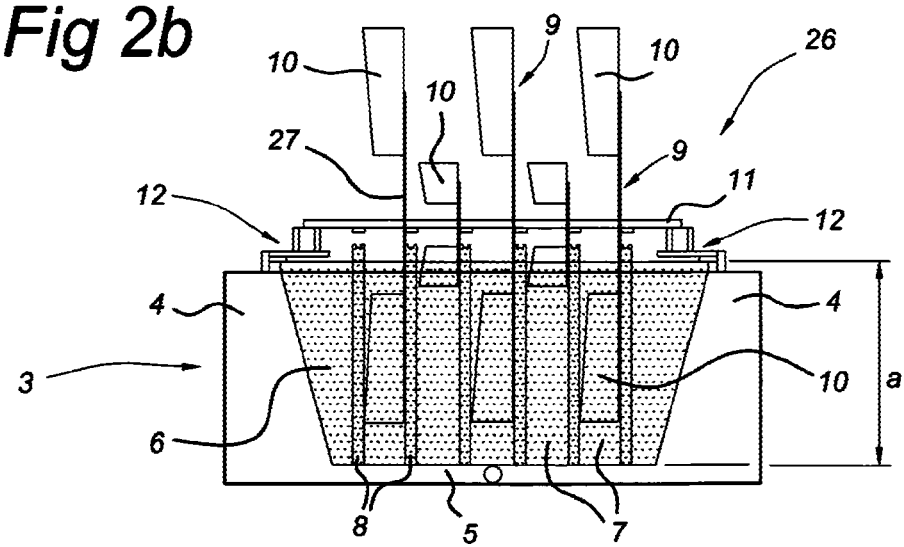
FIG. 2B schematically depicts in cross section an embodiment of a vessel and a harvester system comprised in the bioreactor system according to the invention.

FIG. 2A (top view) and 2B (cross section; front view) schematically depict an embodiment of a pond 3 or vessel 3 and a harvester system 26 comprised in the bioreactor system 1 according to the invention. The vessel walls 4 and vessel bottom 5 make up the vessel 3 that contains the aqueous liquid 6. The vessel 3 is divided in canal sections 7 by the partitions 8.

The harvester system 26 is arranged to extend over the vessel 3. It is conceivable that a harvester system 26 extends over a plurality of vessels 3. The harvester system 26 may be movable connected with the vessel 3, more specifically with the vessel walls 4, even more specifically with the partitions 8. In a specific embodiment the harvester system 26 is movable connected with the vessel 3 by means of a carrier 12, more specifically by means of two opposing carriers 12. The carriers 12 may be guided along the vessel wall 4 by means of a rail 13 or slide way 13. This rail 13 or slide way 13 may also advantageously comprised by the top surface of the partitions 8 (see below).

In this schematically depicted embodiment, the harvester system 26 comprises a plurality of paddle wheels 9. A paddlewheel 9 is arranged to extend during use (at least part of the time) at least partly into the aqueous liquid 6, more specifically a paddle wheel 9 is arranged to extend during use (at least part of the time) substantially half into the aqueous liquid 6. The paddle wheel 9 here comprises an elongate wheel member 27 that rotates around a horizontal rotation axis 11. Furthermore the paddle in an embodiment comprises a scoop 10, specifically two opposing scoops at the extremities of the wheel member 27. It is conceivable that the paddle wheel 9 comprises a plurality of wheel members 27. The scoop 10 scoops aqueous liquid 6 that contains the photosynthetic culture, such as algae. During harvesting the scoop 10 dewaters by means of a sieve (see for instance FIG. 4). The sieve may have a mesh grid of meshed selected from the range of about 0.5-35 μm, such as 0.5 to 10 μm (diameter) to separate the mature photosynthetic culture from the premature photosynthetic culture and the water. The mesh grid of the sieve may determine the size of the harvested photosynthetic culture and partly the harvested fraction consequently determining overall growth conditions and thus yield of the bioreactor system. The mesh size may also depend upon the specific photosynthetic culture.

In an embodiment of the photo bioreactor system 1, the system further comprises a $CO_2$-applicator to supply $CO_2$ to the aqueous liquid. In a specific embodiment the applicator is a $CO_2$ cushion (not shown in this FIG. 2B, but see FIG. 6) extending over the vessel bottom 5. The cushion is provided with a plurality of orifices to dispense and dissolve the $CO_2$ in the aqueous liquid and at the same time create turbulence therein. The preferred way of adding the $CO_2$ is in a solubilized form. More specifically, the $CO_2$ is absorbed in a liquid which is added to the raceway by the applicator. The $CO_2$ is added in such a form that the liquid is always saturated with $CO_2$. The addition of $CO_2$ absorbed in a liquid will minimize the occurrence of gaseous bubbles. This will avoid the occurrence of shear stress in the aqueous liquid.

Figure 10:
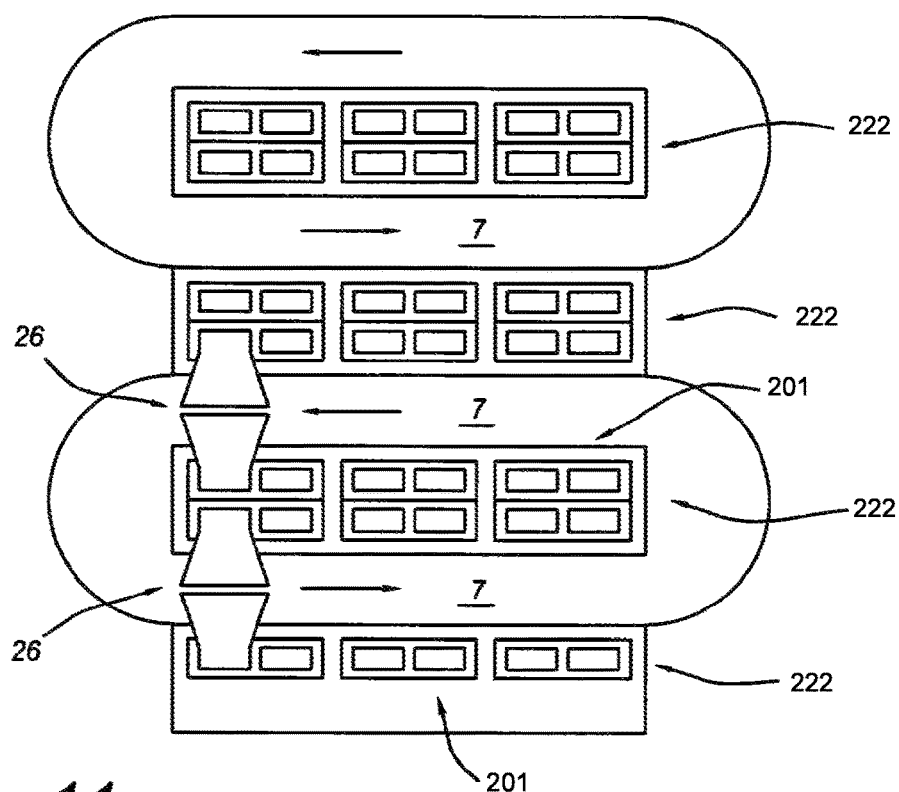
FIG. 10 schematically depicts in perspective view a number of walls comprising lighting panels.

Canal sections 7 may in an embodiment be in liquid contact with each other, such as schematically depicted in FIGS. 8 and 10.

The harvester system 26 as in FIG. 2A may serve each canal section 7 or raceway, but the harvester system 26 may also serve alternating canals. The harvester system 26 may also serve adjacent canals. Since the canal sections 7 may be in liquid contact, flow generated in a first canal section 7 may also generate a flow an second canal section in liquid contact with the first canal section. In this way, it is not necessary that the harvester system 26 serves each canal section.

Figure 3:
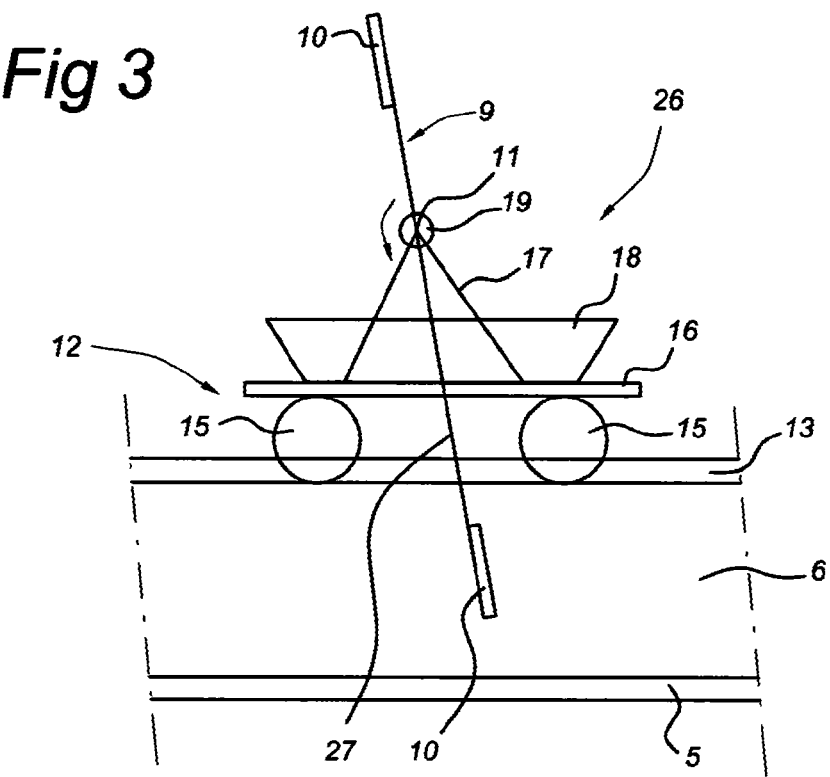
FIG. 3 schematically depicts, in side view, an embodiment of the harvester system comprised in the bioreactor system according to the invention.

FIG. 3 schematically depicts, in side view, an embodiment of the harvester system 26 comprised in the bioreactor system according to the invention. Reference numbers refer to the same parts as in other figures, mainly added numbers will be elucidated. At the centre of a paddle wheel 9 the harvesting system 26 comprises a collector system 18 comprising a container 18. The collector system 18 may be connected to the harvesting system 26 by means of frame members 16, 17, 19. In a specific embodiment the container 18 is provided with dewatering means, more specifically a sieve. For instance, the bottom of the container 18 may comprise a sieve, especially arranged to allow water escape but keep the photosynthetic culture in the container 18. The wheels 15 that run in (or on) the rail 13 enable the harvester system 26 to move with respect to the aqueous liquid 6.

Alternatively or additionally, the collector system 18 may comprise a gutter, which may for instance be arranged sideways. The harvesting system may be arranged to allow the harvested product to slide or fall in the gutter. For instance, the gutter may be arranged on part of wall 4.

Figure 4A:
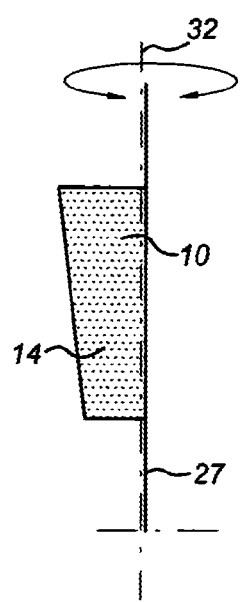
FIG. 4A schematically depicts in side view an embodiment of a scoop comprised in the bioreactor system according to the invention.
Figure 4B:
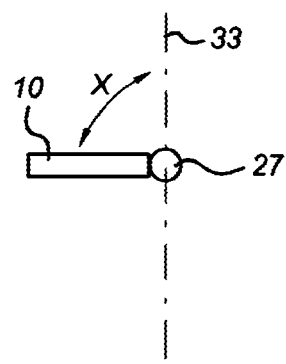
FIG. 4B schematically depicts in top view the scoop of FIG. 4A.

FIG. 4A and FIG. 4B schematically depict an embodiment of a scoop 10 comprised in the bioreactor system according to the invention. The scoop 10 comprises a sieve member 14 with a mesh grid, for instance in the range of 0.5 to 10 μm, or larger, such as in the range of 0.5-35 μm. In fact the mesh size can be in the range of 0.5 to more than 6 μm depending on the culture. The position of the scoop 10 can be adjusted to influence the fraction of the culture that is harvested and/or the amount of turbulence caused by the movement of the scoop 10 in the aqueous liquid 6. The position of the scoop 10 may be adjustable with respect to the elongate wheel member 27 by rotating the scoop around axis 32. The projected surface of the scoop 10 that engages the aqueous liquid may further optionally be adjusted by controlling the angle X that the scoop 10 makes with axis 33, which is an axis perpendicular to axis 32.

FIGS. 5A-C schematically depict an embodiment of a lighting system 24 comprised in the bioreactor system according to the invention. The lighting system 24, or more specifically the lighting panel 28 (also indicated as panel) is arranged in the partitions 8 or comprised by the vessel walls 4 (or both). In an embodiment, the lighting panels 28 are the partitions 8. A vessel may comprise a plurality of panels 28 to irradiate the aqueous liquid 6 (through the entire vessel 3). Since par radiation may only penetrate the aqueous liquid in a limited way, the height of the lighting panel 28 and the depth of the vessel 3 may substantially correspond. A lighting panel 28 may comprise one or more light sources 20, more specifically one or more fluorescent light sources 20 (schematically depicted) and/or one or more incandescent lamps (bulb) (not depicted) and/or one or more LEDs, like LED bars 23 (schematically depicted) with a series of separate LEDs 34.

To scatter and direct the light into all the aqueous liquid the lighting panel 28 may be provided with a reflector 22. E.g. reflectors 22 are provided at the top and/or the bottom of a lighting panel 28. In a specific embodiment the reflector 22 is rotatably connected with the lighting panel 28, more specifically the reflector 22 is rotated by an actuator (not shown), and may rotate around a rotation axis 25.

In an embodiment of the photo bioreactor system 1, the lighting system 24 comprises a rail 13 that is arranged to guide the harvester system 26 of FIG. 3. In this embodiment, the rail 13 is provided on top of the lighting panels 28 (which, as mentioned above, may be arranged as partition 8). The rail 13 may optionally be provided with sides 36 to guide the harvester system 26, especially its wheels 15. In this way, the harvester system 26 may ride over the partitions 9, especially over the (tops of) the lighting panels 28.

The rail 13 may comprise louvers 37 to allow ventilation of the lighting system 24, more specifically of a lighting panel 28, and thereby contribute to cooling of the light sources 20. A lighting panel 28 may comprise a heat sink to transport heat to the aqueous liquid 6 and contribute to the cooling capacity of the lighting panel 28. In a specific embodiment the lighting panel 28 comprises an inlet 38 and an outlet 39 to provide the lighting panel 28 with a cooling liquid that removes heat from the lighting panel 28, for instance to a heat exchanger 40. In a more specific embodiment the cooling liquid comprises water, and in a further embodiment, does not comprise the aqueous liquid 6. The heat exchanger 40 may further be arranged to (evenly) distribute heat in the liquid 6, or provide the heat to a heat storages system (not depicted) that may be used to provide heat to the liquid 6 at periods that heating is necessary (for instance during the night).

In an embodiment of the photo bioreactor system 1, the harvester system 26 comprises a cleaning unit (not depicted) arranged to clean the lighting system 24, more specifically the lighting panels 28, so to enhance even more the irradiation of the photo synthetic culture. Even more specifically a cleaning unit comprises detachable brushes. For instance, the scoops may be arranged to be equipped with a detachable blade and/or brush type material/device to rub against the light panels to keep them clean against fowling or accumulation of any kind of organic growth and/or build up for optimal photosynthesis through the panels.

FIG. 6 schematically depicts in cross section a detail of an embodiment of a vessel comprising a $CO_2$-applicator 29 to supply $CO_2$ 30 to the aqueous liquid 6. In a specific embodiment the applicator 29 is a $CO_2$ cushion 29 extending over the vessel bottom 5. The cushion 29 is provided with a plurality of orifices 31 to dispense and dissolve the $CO_2$ 30 in the aqueous liquid 6 and at the same time create turbulence therein.

The growth condition for the photosynthetic culture is a function of a group of parameters comprising the speed of the harvester system, the speed of the paddle wheel, the angle of the scoop, the mesh of the sieve, the lighting system. At least all these parameters contribute to a controlled environment to maintain the photosynthetic culture in a steep part of the growth curve. Hence, an advantageous aspect of the invention is the freedom to control al kind of parameters, and thereby influence the growth and choose the best conditions, for instance depending upon the latitude of the photo bioreactor, the type of photosynthetic culture, the temperature, etc.

Embodiments of flow enhancement systems 100 will be described referring to FIGS. 7 and 8. FIG. 7 schematically depicts in perspective view some embodiments of flow enhancement systems 100. FIG. 8 schematically depicts in top view embodiments of flow enhancement systems 100.

The flow enhancement system 100 may comprises a flow enhancement body 102 provided with a profile 103 for engaging the aqueous liquid 6 for introducing turbulent flow in the aqueous liquid 6. In an embodiment, indicated with reference 102, the flow enhancement body comprises a funnel (further indicated as flow enhancement body or funnel 102). Flowing liquid may enter inlet 107 and leave outlet 108, with increased speed. Hereby, turbulence may be introduced.

Here, by way of example, the flow enhancement system 100 comprises a plurality of bodies flow enhancement bodies 102, having a funnel type structure, for engaging the aqueous liquid 6 for introducing turbulent flow in the aqueous liquid 6. Alternatively or additionally, the flow enhancement system may comprise an obstacle.

In another embodiment, the flow enhancement body 100 comprises an obstacle 104, such as a cylinder for engaging the aqueous liquid, with for instance cylinder wall 103 of the cylinder. The cylinder wall 103 is also referred to as profile 103.

In a specific embodiment, the reactor 3 comprises a plurality of flow enhancement bodies. In a further embodiment, the reactor comprises combinations of a funnel 102 and an obstacle 104, wherein the obstacle 104 is arranged in line with the outlet 108 of the funnel 102. This may even further enhance turbulence.

Here, the flow enhancement body 102 comprises a conduit 105 for passing fluid from an inlet 107 to an outlet 108 of the conduit 105. The profile 103 may comprise a fluid inlet 107 coupled with the conduit 105 for passing the aqueous liquid 6 through the conduit 105. Alternatively, the inlet 107 may be coupled with a supply conduit 110 for supplying fresh water, nutrients and the like to the aqueous liquid 6. Here, the flow enhancement body 102 comprises a further inlet 109 for fluid coupling the conduit 105 to the supply conduit 110. The fluid may be the aqueous liquid 6, of a mixture of aqueous liquid 6 and the fresh water from the supply conduit 110. Here, the outlet 108 directs the fluid towards a neighboring flow enhancement body 102. Here, the outlet 108 directs the fluid upwards for preventing agglomeration of algae at the bottom of the vessel 3. In this connection upwards means towards the surface of the aqueous liquid 6 contained in the vessel 3 of a photo bioreactor system.

FIG. 8 (top view) schematically depicts embodiments wherein the obstacle 104 is arranged horizontal (bottom left) and vertical (top left), and wherein a funnel 102 is arranged.

In a specific embodiment, the obstacle(s) 104 may further comprise one or more light sources. Since the obstacle 104 is arranged within the reactor, and its obstacle surface is enclosed by water, these light sources may further be used to illuminate the organisms in the liquid. Especially, since red may penetrate further into the liquid than blue, the walls may comprise blue and red emitting light sources, whereas the obstacles may especially comprise blue emitting light sources. Hence, the obstacles may also have the function of auxiliary light source.

It is another aspect of the invention to provide a photo bioreactor system comprising a flow enhancement system 100 according to the invention.

Figure 9A:
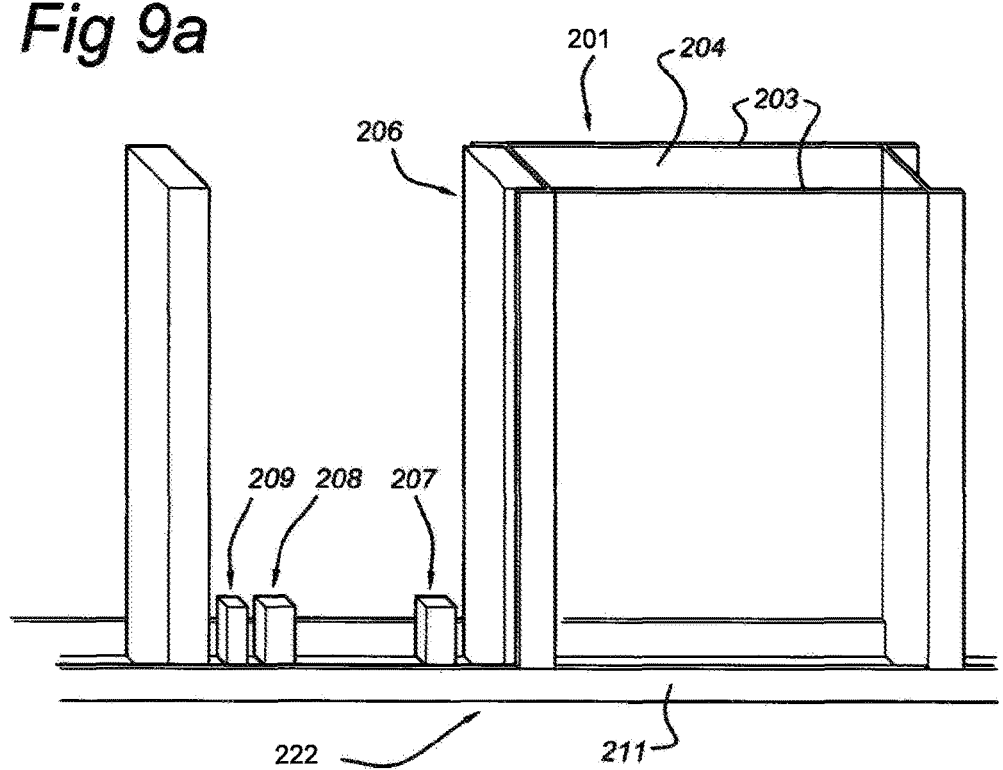
FIG. 9A schematically depicts in perspective view a wall comprising lighting panels.
Figure 9B:
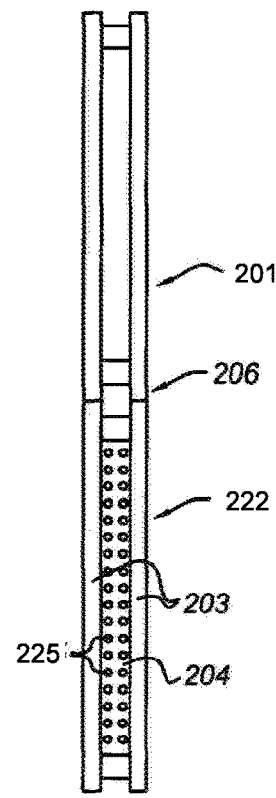
FIG. 9B schematically depicts in top view the wall of FIG. 9A.

The lighting panel 201 will be described referring to FIGS. 9A, 9B and 10. FIG. 9A schematically depicts in perspective view a wall 222 comprising lighting panels 201. FIG. 9B schematically depicts in top view the wall 222 of FIG. 9A. FIG. 10 schematically depicts in perspective view a number of walls 222 comprising lighting panels 201.

The lighting panel comprises transparent sidewalls 203 forming a compartment 204, a light source 225 provided in the compartment 204 for lighting the algae, coupling means 206 for accommodating the lighting panel 201 in a wall 222 comprising coupled light panels 201, and optionally connection means and/or power supply, indicated with references 207-209. The wall 222 comprises coupled light panels 201 and is suitable for forming canal sections 7, also known as raceways 7, in a vessel of the photo bio reactor system.

Here, the compartment 204 comprises a plurality of light sources 225, more specifically each of these lights sources 225 provide light with a specific wavelength, even more specifically the light source 225 or sources 225 comprise a light emitting diode.

In a specific embodiment of the wall, the wall comprises a frame 211 for coupling and supporting the light panels 201.

In an example of the invention a photosynthetic culture may be grown in a vessel containing an aqueous liquid (especially water) (comprising this photosynthetic culture), more specifically a series of vessels enclosed in a controlled and/or closed environment, such as a greenhouse that provides a controlled environment to optimize the growth condition for the photosynthetic culture. The culture is continuously harvested by the harvesting system that may scoop approximately up to about 10 wt % of photosynthetic culture per day; lower amounts of harvesting may also be applied, such as up to about 1% or up to about 0.1%, or up to about 0.01% culture per day. For that reason the scoop comprises a sieve with an appropriate mesh to harvest the mature culture and leave the aqueous liquid and the remaining culture in the vessel. Furthermore the harvester system is provided on a harvester transporter that moves the harvester over the entire vessel to provide an even harvesting of the entire vessel. The harvested culture is collected by a collector system that conveys the culture to a depot.

Harvesting of the photosynthetic culture with a scoop has a benefit of contributing to turbulent flow in the aqueous liquid. The turbulent flow contributes to optimal growth condition for the photosynthetic culture. Turbulent flow is also generated by a $CO_2$-applicator that dispenses $CO_2$ at the bottom of the vessel and whereupon the rising gas bubbles contribute to turbulent flow in the aqueous liquid contained in the vessel. Turbulent flow may also be generated by a $CO_2$-applicator, that dispenses an additional stream, comprising at least $CO_2$, nutrients, salts, at the bottom of the vessel and whereupon the rising stream contributes to turbulent flow in the raceways.

Growth conditions for the photosynthetic culture are further enhanced by the lighting system that contributes to irradiation of the photosynthetic culture in the aqueous liquid. The light source comprised in the light system, irradiate the culture throughout the whole vessel, especially with respect to the deeper parts of the vessel. Reflectors, especially rotating reflectors, contribute to an even distribution of the light through the whole vessel.

The light panels may make up the walls that divide the ponds into (numerous) raceways, the number of which will depend on the desired distance required between the light panels to obtain the optimal light penetration in a specific density for optimal growth for any particular species of algae and the optimal dynamic flow desired.

A frame or structure may be securely mounted on the floor of the pond to receive and hold the light panels which could comprise waterproof fittings and/or fixtures to supply each of the individual light panels with power and coolants.

The light panels may be waterproof either sealed or with a removable cap and can be fitted with inlets for coolant and power supply and outlets for coolants.

There may be different liquids used in the light panels, one for the transmission of light within the light panel another may be used and circulated only for cooling the lights.

In an embodiment, mountable light panels that can be integrated with the glass wall of the raceway.

For optimal algae growth, light of a specific color (wavelength(s) or wavelength range(s)) may be provided to the raceways.

To be able to provide light with a specific color use may be made of light panels that consist of a light source or sources providing different colors.

The light panels can be inserted in the walls of the raceway, and comprises a number of light sources. In this way the intensity, wavelength, and the spatial distribution of each specific color of light in the medium can be optimized.

The size of the panels may for instance be fixed by about 2 by 1=2 $m^2$, but the number of light sources per panel can be adjusted to different applications i.e. type/strain of algae and type of growth medium. More specifically:

a) the number of light sources per panel can be adjusted, e.g. for every two red light sources there are eight blue light sources, b) the size and/or intensity of the light source for each color can be adjusted, and c) the distance between the light sources can be adjusted.

The panels comprise at least two light sources that produce a different color. The light sources for the different colors include a light source that produces blue light (400-500 nm or more specifically 400-450 nm) and red light (600-730 nm or more specifically 640-680 nm). In an embodiment, the light sources are LED (light emitting diode) lamps. The light intensity of the light sources, the photon flux density (PFD) may be up to 2000 micromole photons per square meter per second ($\mu mol$ photons $m^{-2}$ $s^{-1}$). Furthermore, by adjusting the distance between and/or the number of 'columns with light sources' (in each panel) the effective exposure time (of the algae) to a light with a specific wavelength can be controlled.

Optimization of the high intensity-low intensity cycle can be achieved by adjusting the number of light sources per unit of length and the (circulation) flow rate of the main flow. Typically, the main flow rate will be in the order of 0.6 m/s, the average PDF will be between 50 and 500 ($\mu mol$ photons $m^{-2}$ $s^{-1}$) while the exposure time for the maximum light intensity the will not exceed 5 ms.

In order to maintain a constant circulation flow of the algae suspension additional injection points may be needed along the length of the raceways. In the case that the circulation rate of the algae suspension is too low, the algae may start to settle and agglomerates will be formed, which is detrimental for the algae.

To avoid the settling of the micro-algae, upwelling by an extra liquid flow will be used, the extra liquid flow may be entered in the raceways by so-called injection point or flow enhancers.

The purpose of the injection points may in an embodiment be two-fold. First, the injection points may be used to add one or more of fresh water, nutrients, $CO_2$ and optionally other ingredients required for a constant growth of the algae.

Second, by controlling the direction of the flow and by controlling the flow rate so-called upwelling will be induced. The direction of the extra liquid flow this will be determined by the angle of the injection point and the location of the injection point. The injection point can be placed perpendicular to the flow in the raceway or the injection points can be placed under an angle.

The injection points may be located in the bottom of the raceway (bottom flow enhancers) and in the wall of the raceway (side flow enhancers). For the flow enhancers placed under an angle in the wall, the angle is such that an upward flow is achieved.

In an embodiment, the liquid flow is added at an elevated pressure of 1-15 bars (per surface). In this way, the pressure difference between the main flow and the locally introduced extra liquid flow will affect (locally) the motion of the algae. The liquid at an elevated pressure may cause motion and suction of the algae. This phenomenon is known as the Venturi effect.

More specifically, the additional flow (provided by the flow enhancers) can be adjusted to the viscosity of the algae suspension. In this way, the circulation velocity can be increased. If required, a pumping system can be used to deliver the additional liquid flow with a specific flow rate and with a specific density and viscosity.

For a constant and stable growth rate of the algae, it is important that lighting conditions, for exposing the algae, are controllable. To achieve this radial movement of the algae transverse to the lighting panel is beneficial, that is the algae should move from the center of the raceway to the wall of the raceway, and move back to the center. At the same time, of course, movement along the length of the raceway (axial movement) should take place to avoid settling.

Additional movement in the radial direction, also known as swirls or swirling, will be induced by make use of internals or static mixtures along the length of the raceway. Swirl flow is a steady rotational flow around an axis.

A possible construction consists of a 'cylindrically-shaped' internal erected in the main flow. One possible approach will be based on a cylinder, e.g. located at the centerline of the raceway. In this way the main flow will be "split in two" and as a result at both sides (of the axial centerline) a swirl will be formed. These swirls will assure radial motion and the algae may move, in a continuous circular motion, from the center of the raceway to the wall and back to the center.

More sophisticated solutions are also possible by using so-called static mixers which will assure radial motion and upwelling at the same time. The cylindrical shaped construction, which is used as obstacle (see also above), may be arranged horizontal, vertical or under an angle with the bottom of the reactor. Especially, they are arranged horizontal or vertical, in an embodiment one or more are arranged vertical.

Also, the internals can be used to provide additional underwater lighting from the center of the raceway by equipping the internals with light sources. In particular, the internal can have LED lights as well to create an optimal light mix and growing environment in the middle of the raceways.

In this way, an additional 'parameter' is available for fine-tuning the relation between the flow rate (actually the size of the raceway in terms of (both) the length and the width) and the light intensity (high-low intensity cycle). Equipping the internal with light panels will lead to a more flexible design, because the size of the raceway is longer determined (solely) by the penetration depth of the light sources located at (or in) the walls of the raceways.

In a specific embodiment, the one or more scoops of the harvester are rotatable around a scoop axis and/or can be subjected to vibrations with a vibration apparatus and/or may be subjected to an air flow, especially when the respective scoop is above the liquid's surface, with an air blower, and/or may be sprayed by water, especially when the respective scoop is above the liquid's surface, with washer apparatus, and/or may be subject to back washing, for instance by a liquid flow generator. Such embodiments may be used to remove remaining solids at the scoop, especially in/on the meshes. In this way, a kind of backwashing may be provided to the scoop, especially the sieve scoop.

In the embodiments described and depicted herein, optionally, the harvester system may be replaced by a paddle wheel construction "only", i.e. the paddle wheel construction is not used as harvester system, but is substantially only used to create turbulence, especially flow. Hence, in specific embodiments, unless clear from the context, the harvester system 26 may relate to a paddle wheel construction that is arranged to create turbulence in the liquid, and is not especially arranged to harvest culture.

The herein describe technologies will also be indicated as ALGAE-SPHERE™.

The driving forces behind the ALGAE-SPHERE™ concept are
- Increase biomass productivity per unit of time, volume and surface area and as a result per invested capital
- Increase the net yield of algae products, like oil, vitamins, anti oxidants, etc
- Decrease the investment risk with cost efficient production
- Make use as much as possible of proven, simple and robust technologies
- Controlled production independent from climate and environment
- Modular and commercially up-scalable.

The ALGAE-SPHERE™ production facility has the advantage of using natural solar irradiation with a production potential of approximately 150 t/ha/year, complemented by a specifically ALGAE-SPHERE™ designed grow lighting technology. The lighting efficiency can be as high as 30 to 50% of PPF density of the lighting system and the natural light. The effective PAR surface area in a typical ALGAE-SPHERE™ facility is increased with 270% compared to an open pond system and many more times compared to PBRs. The lighting quality and quantity is adjustable depending on the algae growth and development requirements and the products to be obtained. The resulting production potential is increased dramatically compared to other algae production technologies.

One or more advantages may be:
- In an ALGAE-SPHERE™ the process conditions can be optimized for almost every species imaginable and desired algae product;
- The ALGAE-SPHERE™ production facilities typically consists of a modular system, with a base module of 1 hectare, the system is practical, manageable and can be expanded to hundreds of hectares;
- A single module itself consists of 20 individual production units and can be fully separated from each other for production flexibility;

A single module can handle various production objectives, using different algae or maintaining different growth conditions in each of the separate units;

Food, feed and/or pharmaceutical quality in an up scaled system;

Productivity per square meter under fully optimized light climate has the potential to be 5-times higher than the closed PBR and as much as 10 times that of open pond systems;

Latest most efficient LED technology;

Latest engineering and technologies for easy operating and low maintenance;

$CO_2$ of different industrial sources can be captured and fed in high concentrations to the algae, without causing shear stress damage to the cells;

Energy efficient harvest technology; and

Potential for cost reductions by cradle to cradle solutions for energy, $CO_2$ and effluents.

Figure 11A:
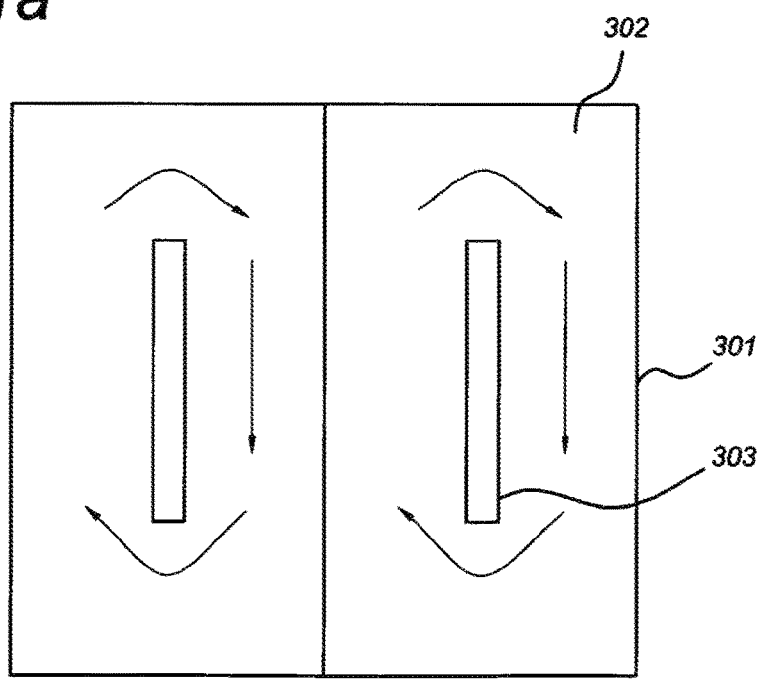
FIG. 11A is a simplified top view of an embodiment of a bioreactor with light panels.
Figure 11B:
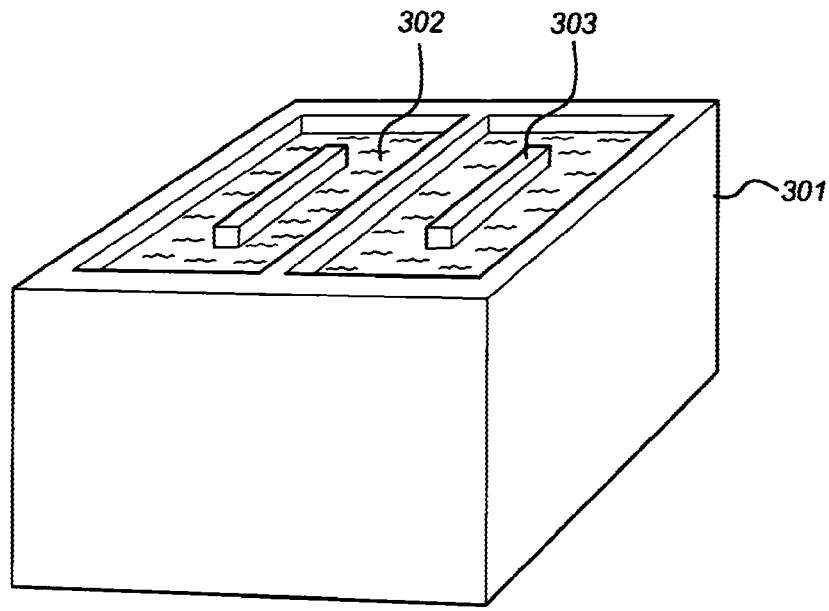
FIG. 11B is a perspective view of the bioreactor of FIG. 11A.

FIG. 11A is a simplified top view of an embodiment of a bioreactor with light panels, and FIG. 11B is a perspective view of the bioreactor. The bioreactor 301 comprises a vessel, further referred to as tank 301, containing an aqueous liquid in which algae or other photosynthetic culture is grown. The aqueous liquid may be fresh water or salt water or some other suitable aqueous solution, but for simplicity is referred to herein as water. The photosynthetic culture may be algae or cyanobacteria or another other suitable photosynthetic organisms, but for simplicity is referred to herein as algae.

The lighting panels 303 are at least partially submerged in the water. This enables much more of the light emitted from the lighting system to be transmitted into the water, by emitting the light from the walls of the lighting panel at a point below the top surface of the water. The lighting panels may be used as walls within the bioreactor to form canal sections, further referred to as raceways 302. When the lighting panels are used as walls, they may be securely mounted on the floor of the bioreactor. Alternatively, adjacent raceways 302 may be in liquid contact with each other. The use of lighting panels 303 submerged in the water permits improved and more flexible transmission of light into the water by arranging the panels closely enough so that the light reaches most of all of the algae in the volume of water in the tank.

The bioreactor may be divided into a number of raceways, the number and size of which may depend on one or more of the size of the panels, the size of the bioreactor, the penetration depth of the lighting used in the lighting panels, and the specific species of algae being grown within the bioreactor. The use of raceways enables controllable movement of the algae such that light supplied from the walls is evenly distributed over the algae in the water. Such movement may include a movement around the light panel wall, for example in a clockwise or anti-clockwise fashion, as well as an alternating top-down movement of the algae.

The use of artificial light inside the bioreactor tank avoids the need to construct the tank from a transparent material. This reduces cost and enables the bioreactor tank to be made from cheaper and more durable materials, and results in tanks that are more easily fabricated. The bioreactor tank may be made, for example, from steel, stainless steel, and the like.

The tanks may also be much taller than a pond or traditional bioreactor dependent on sunlight. This enables tanks to have a much smaller footprint for the same volume of algae culture, saving ground space and enabling a much more compact algae growth facility. This has particular importance in urban environments or where land costs are high.

Accurate temperature control of the water in the tank is also more easily achieved with the bioreactor of FIGS. 11A, 11B. A bioreactor relying on exposure to sunlight requires a large surface area. A more compact arrangement with less surface area reduces the effect of outside temperature variations, and non-transparent tank walls reduce the temperature variation due to variations temperature and sunlight from day to night and summer to winter.

Accurate control of the light received by the algae is also more easily achieved with the bioreactor of FIGS. 11A, 11B. Ponds or bioreactors relying on sunlight are subject to wide variations in light exposure, between night and day, sunny or cloudy conditions, long summer days or short winter days. By using artificial light, the light exposure period is increased to 24 hours per day, and constant lighting is provided throughout the year regardless of outside conditions. The lighting system can be tailored to provide light in the specific wavelengths which can be used by the algae for growth. The lighting system can also be tailored to provide light at the right intensity to achieve high growth rates, while avoiding excessive exposure which harms the algae.

Figure 12:
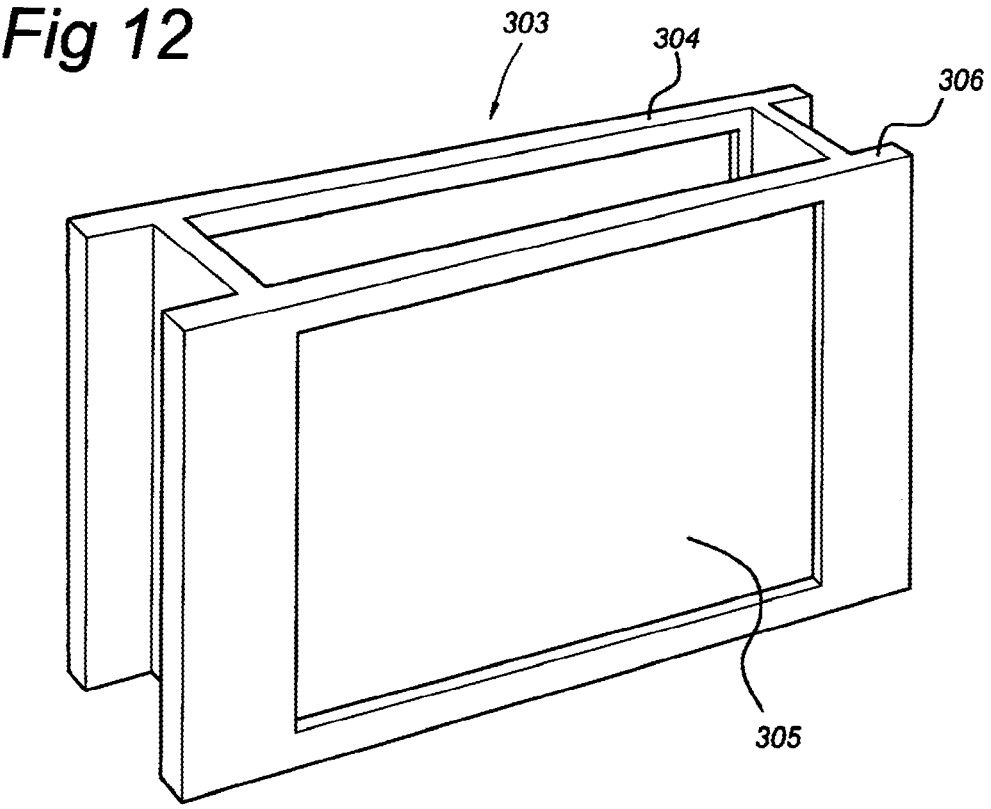
FIG. 12 is a perspective view of an embodiment of a lighting panel.

FIG. 12 is a perspective view of an embodiment of the lighting panel 303. The lighting panel has a housing comprising a frame 304 with transparent walls 305. Alternatively, the frame itself can be constructed of a suitable transparent material. The transparent walls 305 may be made of glass, polycarbonate, or other suitably strong transparent material. In an embodiment, the transparent material like glass has a refractive index of 1.3 or higher.

Figure 13:
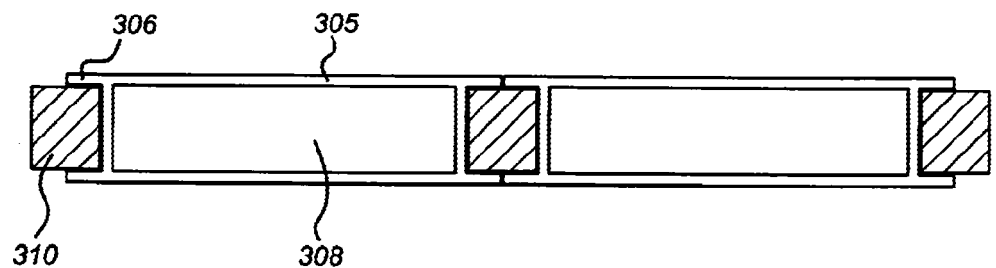
FIG. 13 is a top view an arrangement of lighting panels in a bioreactor.

FIG. 13 is a top view an arrangement of lighting panels in a bioreactor. The lighting panels have a coupling arrangement 306, in this embodiment in the form of flanges, to couple the lighting panels together to form a wall section in the bioreactor. The flanges 306 cooperate with a beam or pillar 310 to locate the lighting panel. This results in an arrangement in which the lighting panels slide vertically into place in the bioreactor. A wall composed of several lighting panels arranged end-to-end may be formed in this way, e.g. with the interface between lighting panels forming a smooth wall to avoid impeding the flow of water along the length of the wall formed by the panels. The lighting panel is waterproof, so that an interior cavity 308 in formed in the lighting panel 303, separated from the water in the bioreactor when the lighting panels are placed into the water.

The lighting panel 303 may comprise an arrangement of LEDs 320. The expression LEDs in this context also refers to LED chips or LED dies. The LEDs 320 may be mounted on a ceramic carrier like a ceramic printed circuit board, which is mounted on a mounting structure within the lighting panel 303. In an embodiment, the mounting structure is a planar structure. The ceramic carrier may be a metal core PCB to support a large number of LEDs, for example 60 LEDs. The ceramic carrier with naked bonded LEDs may be glued or eutectic bonded on the mounting structure.

The LEDs 320 form a light source for illuminating the algae in the bioreactor tank 301. The light intensity of the light source can be tailored to be of sufficient intensity to substantially prevent growth of the photosynthetic culture or algae on the surface of the transparent portion of the housing. The light source may comprise different types of LEDs, emitting light in certain specific wavelengths most suited to promoting growth of the algae. For example, the light source may comprise a combination one or more LEDs for emitting light with a wavelength in the range of 400-500 nm, or more specifically 400-450 nm (e.g. blue LEDs) and one or more LED for emitting light with a wavelength in the range of 600-730 nm, or more specifically 640-680 nm (e.g. red LEDs). The LEDs for emitting the red light may be an aluminum indium gallium phosphide LED.

In some embodiments, the light source is arranged so that, in operation, most of the light emitted from the light source has a wavelength in the ranges of 400-450 nm and 640-680 nm, e.g. 80% or more. These wavelengths are chosen to match the absorption maxima of chlorophyll and the pigments which are used by various types of algae and photo synthetic organisms to grow.

Figure 14A:
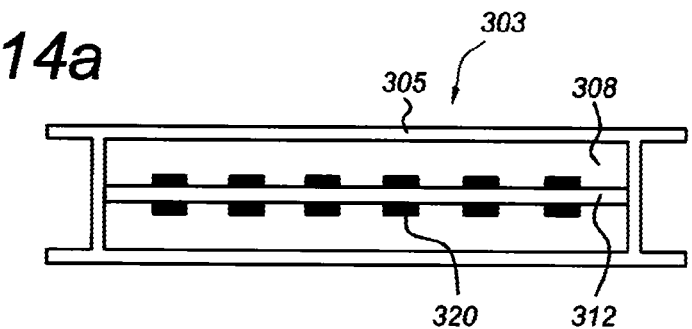
FIG. 14A is a simplified top view of an arrangement of LEDs in a lighting panel.
Figure 14B:
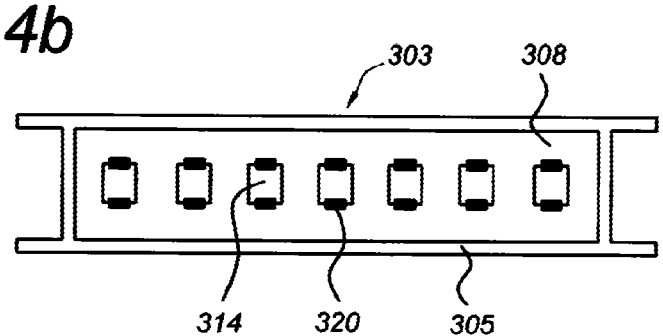
FIG. 14B is a simplified top view of another arrangement of LEDs in a lighting panel.

FIG. 14A is a simplified top view of an arrangement of LEDs in the lighting panel 303. A mounting plate 312 is arranged in a vertical position in the interior space 308 of the lighting panel. LEDs 320 are arranged on the plate to emit light through the transparent walls 305. The mounting plate 312 is e.g. rigid and a good heat conductor, such as aluminum, copper or steel, to conduct heat away from the LEDs which get hot during operation. The interior space 308 may be filled with a cooling liquid 319 in direct contact with the LEDs to transfer heat away from the LEDs. Additionally or alternatively, the plate 312 may be provided with one or more cooling channels for circulation of a second cooling fluid for enhancing the removal of heat from the LEDs. FIG. 14B shows an alternative arrangement of LEDs mounted on mounting struts 314 arranged vertically in the lighting panel.

Figure 15A:
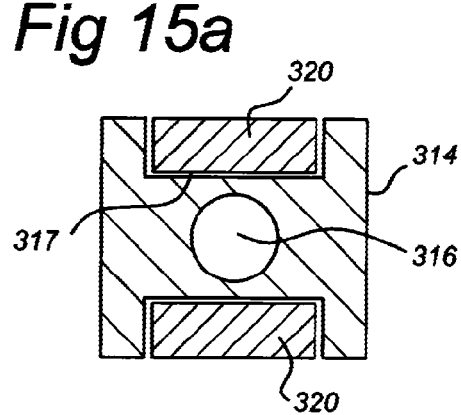
FIG. 15A is a cross-sectional view of a two-sided mounting arrangement for LEDs.
Figure 15B:
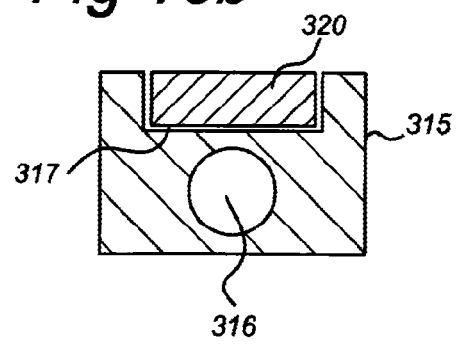
FIG. 15B is a cross-sectional view of a one-sided mounting arrangement for LEDs.

FIG. 15A shows a cross-section of a two-sided mounting arrangement. The mounting strut 314 has an internal channel 316 for circulation of a cooling fluid for cooling the LEDs. The mounting strut may also include a recess 317 on each side in which the LEDs 320 are mounted. This design permits secure mounting of the LEDs which face outwards to emit the maximum light towards the transparent walls 305 on each side of the lighting panel, while providing cooling to the back of the LEDs. The mounting struts are e.g. made from a good heat conductor, such as aluminum or copper, to efficiently conduct heat away from the LEDs. FIG. 15B shows an alternative one-sided mounting arrangement for LEDs.

Figure 16:
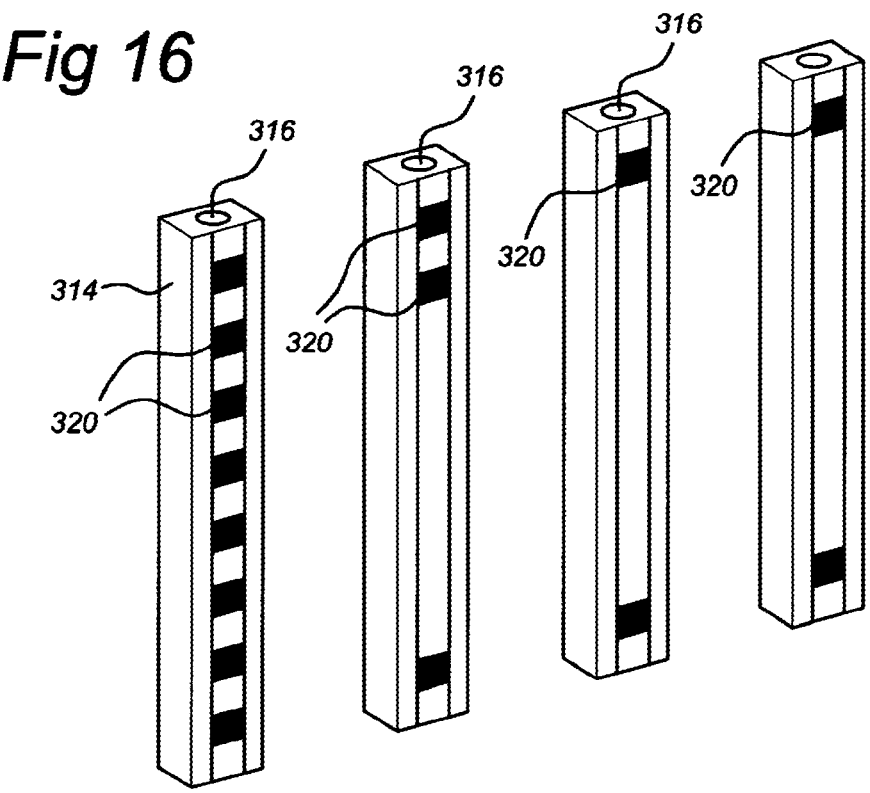
FIG. 16 is a perspective view of a mounting arrangement for LEDs.

FIG. 16 shows a perspective view of mounting struts 314 arranged vertically side-by-side along the length of the lighting panel. The use of mounting struts 314 in a vertical arrangement allows for a more flexible modular construction of the lighting panel, which may be beneficial in terms of flexibility and capability to match the lighting panel requirements with the algae species to be illuminated.

Figure 17:
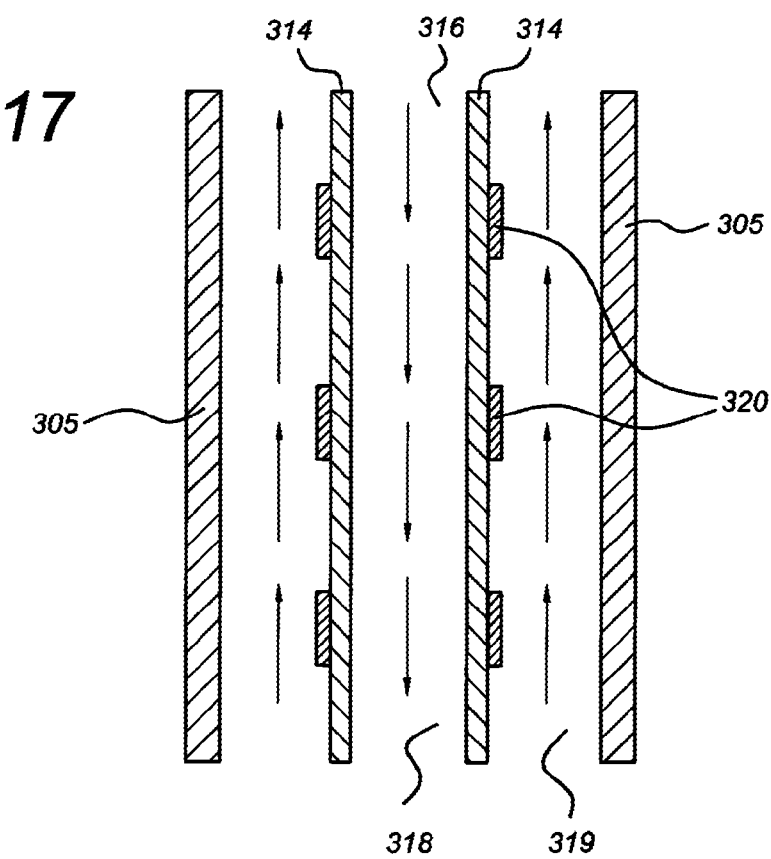
FIG. 17 is a cross-sectional side view of a lighting panel showing circulation of cooling fluids.

FIG. 17 shows a cross-section through the lighting panel and mounting strut showing circulation of the two cooling fluids for cooling the LEDs. The LEDs 320 are mounted on both sides of mounting strut 314, with channel 316 formed in the mounting strut.

All of the above embodiments may use two cooling fluids, a first cooling liquid in direct contact with the front side of the LEDs and a second cooling fluid flowing in a channel to remove heat from the back side of the LEDs. The first cooling fluid will hereafter be referred to as first cooling liquid.

The first cooling liquid 319 fills the interior space 308 between the LEDs 320 and the transparent wall 305 of the lighting panel. This cooling fluid flows past the external front surface of the LEDs, e.g. in direct contact with the LEDs. The cooling liquid 319 is e.g. an oil. The cooling liquid 319 e.g. circulates under natural convection, rising from the bottom of the lighting panel as it gets hotter from contact with the LEDs. The LED chips are e.g. mounted vertically, with the LED's bottom electrode against the mounting plate 312 or mounting strut 314 to promote heat transfer from the LED to the mounting structure. The LED's top electrode faces outwards and is cooled by the cooling liquid 319. The LED dies may be provided with a very thin protection or passivation film, to provide physical protection while still permitting good heat transfer from the LEDs to the cooling liquid. The blue LEDs (emitting in the range 400-450 nm) e.g. have a protection or passivation film, e.g. only on the top surface, to protect them from the cooling liquid 319. The red LEDs (emitting in the range 640-680 nm) e.g. do not have any protection or passivation film, as they are not adversely affected by the cooling liquid.

Forced convection of the cooling liquid 319 may also be used, although excessive flow may damage the bond wires of the vertically arranged LEDs. Furthermore, for this reason, the bond wires of the LEDs 320 e.g. extend in a direction parallel to the flow of cooling liquid 319.

The first cooling liquid 319 is e.g. an oil with a high refractive index, such as DOW CORNING C5 or C51. The lighting system is e.g. constructed of materials selected to have favourable refractive indices to maximize the transmission of light from the LEDs into the water containing the algae. The LED chips typically have a refractive index of about 3.3 for red LEDs and 2.2. for blue LEDs. It is advantageous if the first cooling liquid is in direct contact with the LED and has a refractive index matching the LED as closely as possible. This reduces reflection of light at the boundary between the LED 320 and the cooling liquid 319 to result in the maximum extraction of photons from the LEDs.

A suitable cooling liquid 319 has a refractive index, good transparency, and sufficiently low viscosity to flow easily over the LEDs under natural convection. The first cooling liquid 319 e.g. has a refractive index in the range of 1.5 to 1.7, and specifically up to 1.62. Highly refractive titanium dioxide ($TiO_2$) nano particles, e.g. with a refractive index of about 1.8, may be dissolved in the oil 319 to increase the refractive index of the suspension to about 1.7.

The first cooling liquid 319 also has other advantages. The film of cooling liquid/oil 319 ensures good thermal contact between the LEDs 320, mounting structure 312 or 314, and the transparent wall 305. Wetting of the LED chip's front surface by the cooling liquid 319 improves heat transfer from the LEDs. A suitable cooling liquid 319 also acts to reduce deterioration of the encapsulant of the LEDs. The cooling liquid 319 also enables thinner transparent walls to be used for the lighting panel, especially for deep lighting panels placed in deep water (e.g. 2 m or more) in tall bioreactor tanks, since the cooling liquid pressurizes the interior to the lighting panel to assist in counteracting the external pressure from the water.

The second cooling fluid 318 may be circulated in channels behind the LEDs in the mounting plate 312 or mounting struts 314 to increase the cooling capacity of the system. The cooling fluid 318 may be water, e.g. water that has not been in contact with the water in the bioreactor tank 301. In a preferred embodiment, the cooling fluid has a temperature below 0° C. In such case the cooling liquid 318 may be a refrigerant or a cooled gas, for example cooled carbon dioxide gas. Cooling the LEDs via the channel 316 with a cooling fluid at a relatively low temperature, e.g. below 10° C., e.g. below 0° C., enables the LEDs to operate at a relatively low temperature as well, which will increase the performance of the LEDs 320. Additionally, the possibility to choose the type of cooling fluid 318 may help to adjust the temperature of the water in the bioreactor to a temperature that suits a specific species of algae or photosynthetic culture.

In FIG. 17, the second cooling fluid 318 is circulated in the channel 316 is directed in a direction opposite to the direction of the convective flow of the first cooling liquid 319. Although this arrangement is preferred, it is also possible that the second cooling fluid 318 travels through the channel 316 in a direction that is similar to the direction of the first cooling liquid 319.

The entire construction of the submerged lighting system is e.g. designed to maximize light transmission from the LEDs into the water containing the algae. This is accomplished by matching the refractive indices as closely as possible of the materials through which the light passes from the LEDs to the water containing the algae and avoiding large differences in the refractive indices of these materials. As discussed above, a first cooling liquid 319 has a high refractive index in an ii embodiment to reduce reflection at the boundary between the LEDs and the cooling liquid. The transparent wall 305 is e.g. constructed of a material with a refractive index that approximates or matches the first cooling liquid 319, for example glass with high lead content or any other transparent material like, for example, polycarbonate or epoxies. A typical refractive index of glass is 1.52 which can be increased by the addition of lead to match the preferred range for cooling liquid 19 of 1.5 to 1.7. Water has a refractive index of about 1.33. Thus, matching the refractive indices of the cooling liquid 319 and transparent wall 305 will reduce reflections at that boundary, but may increase reflection at the boundary between the transparent wall and the water containing the algae.

In an embodiment, light emitted by the LEDs does not pass through air before being emitted from the transparent portion of the housing. In such embodiment, the light solely passes through liquid and solid media before such emission. In other words, the submerged lighting system has no low refractive index layer, such as air, between the LEDs and the water containing the algae. Thus, although there is a decrease of the refractive indices of the layers of material through which the light passes, there is no increase. For example, the approximate refractive indices in one embodiment may be: LED 3.3 (red LED) or 2.2 (blue LED), cooling liquid 1.7, transparent wall 1.7 (glass with lead content) or 1.52 (glass without lead) or 1.42 (polycarbonate), and water 1.33. With this arrangement, the lighting panel can achieve improved coupling of light from the LEDs to the water, of 2.5 or more micromoles of photons per watt of power input to the lighting panels. In contrast, lighting systems with an air gap can only achieve values around 1.0 micromoles per watt. A bioreactor with this type of lighting arrangement can achieve algae growth resulting in a doubling of the algae every 6 hours, as opposed to previous systems relying on sunlight which typically achieve a doubling of the algae every 24 hours.

Growth of algae on the outside surface of the transparent portions of the lighting panel housing reduces the effectiveness of the lighting system. This algae adhering to the transparent walls will not circulate in the water and blocks light from the LEDs from reaching the bulk of the algae circulating in the water. This undesirable algae growth can be reduced or eliminated by adjusting the intensity of the light source. In operation, the light transmitted through the transparent walls 305 is e.g. of sufficient intensity to substantially prevent growth of algae on the surface of the transparent walls. A light flux of 1000 micromoles per second per square meter or higher at the outside surface of the transparent wall has been shown to be sufficient for this purpose. The light should not be too intense to prevent harm to the algae circulating in the water.

Figure 18:
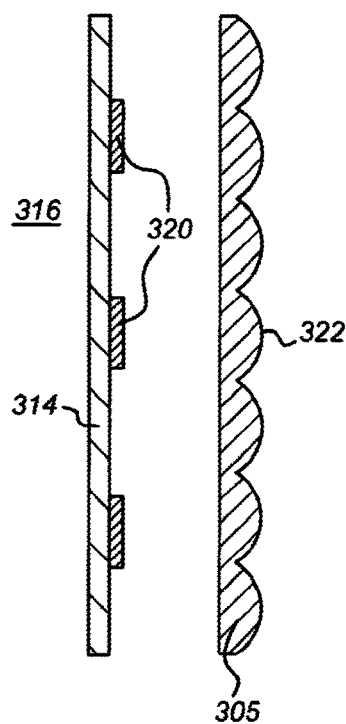
FIG. 18 is a cross-sectional view of a diffuser arrangement.

FIG. 18 is a cross-sectional view of a light panel 305 provided with a diffuser arrangement 322. The transparent walls 305 e.g. include a diffuser arrangement 322 to disperse light from the LEDs 320 into the water. The diffuser arrangement 322 may take the form of convex shapes on the outside of the transparent walls 305 of the housing. Alternatively, or additionally, the diffuser arrangement may take the form of a diffusion film or sheet that is provided on a surface of the transparent walls of the housing.

Figure 19A:
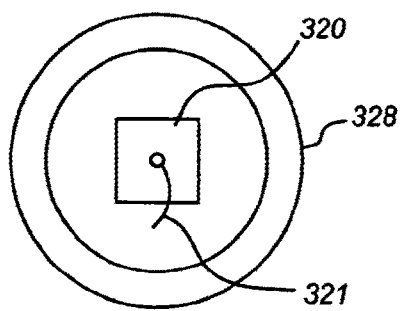
FIG. 19A is top view of a reflector arrangement for LEDs.
Figure 19B:
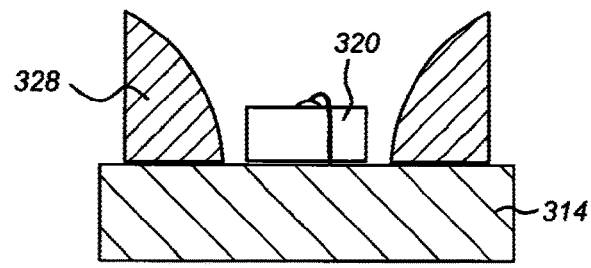
FIG. 19B is a cross-sectional view of a reflector arrangement for LEDs.
Figure 19C:
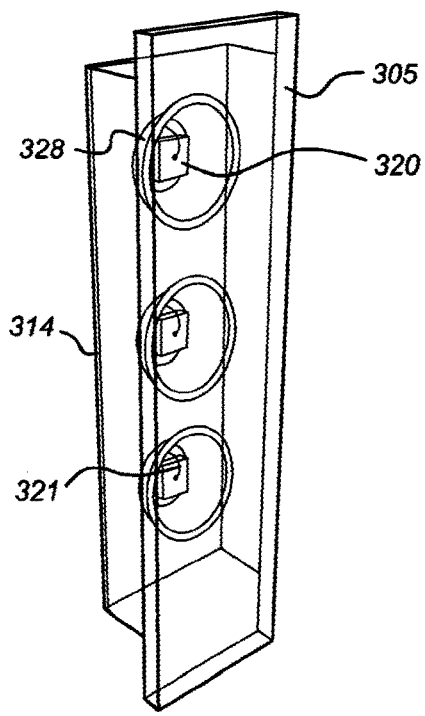
FIGS. 19C and 19C' are perspective views of a reflector arrangement for LEDs.
Figure 19C:
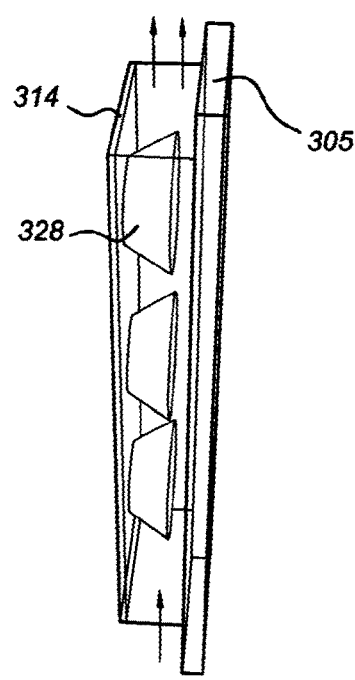

FIG. 19A is top view of a reflector arrangement that may be used in combination with one or more of the LEDs 320, while FIG. 19B shows a cross-section of a specific embodiment of such reflector arrangement. FIGS. 19C and 19C' are perspective views of a reflector arrangement that differs from the reflector arrangement of FIG. 19B. The reflector arrangement comprises one or more reflectors 328 that may be used around the LEDs 320 to increase light transmission from the LEDs into the water, by directing light emitted from LED in direction substantially perpendicular to the transparent wall 305. The one or more reflectors 328 may take the form of concave structures surrounding the LED, for example as a rim structure as shown in FIG. 19B or 19C. The concave structures may be made of a metal, or a material with a low refractive index sufficiently different from the cooling liquid 319 to result in good reflection of light from the LEDs, e.g. an easily formed material like a suitable epoxy, e.g. with a refractive index of about 1.1. The rim structure can be shaped as shown in FIG. 19B to ensure that the combination of shape and refractive index of the rim structure material reflects light emitted by the LED 320. The reflector arrangement in an embodiment comprises a circular reflecting surface surrounding each LED to enhance the uniformity of light emission.

The reflector arrangement can be designed such that it limits the angle at which light is emitted by a LED towards the water. The outer angle at which light emitted by the LEDs is received at the interface between the cooling fluid and the transparent wall may be arranged such that total reflection at this interface, and e.g. also at the interface between the transparent wall and the water, are avoided as much as possible. By limiting the exit angle of the LEDs in such a way, the reflector arrangement reduces efficiency losses due to total reflection. For similar reasons, e.g., the reflector is arranged to reflect light emitted from the LEDs towards the transparent wall of the lighting panel substantially at right angles to the surface of the transparent wall.

Figure 20:
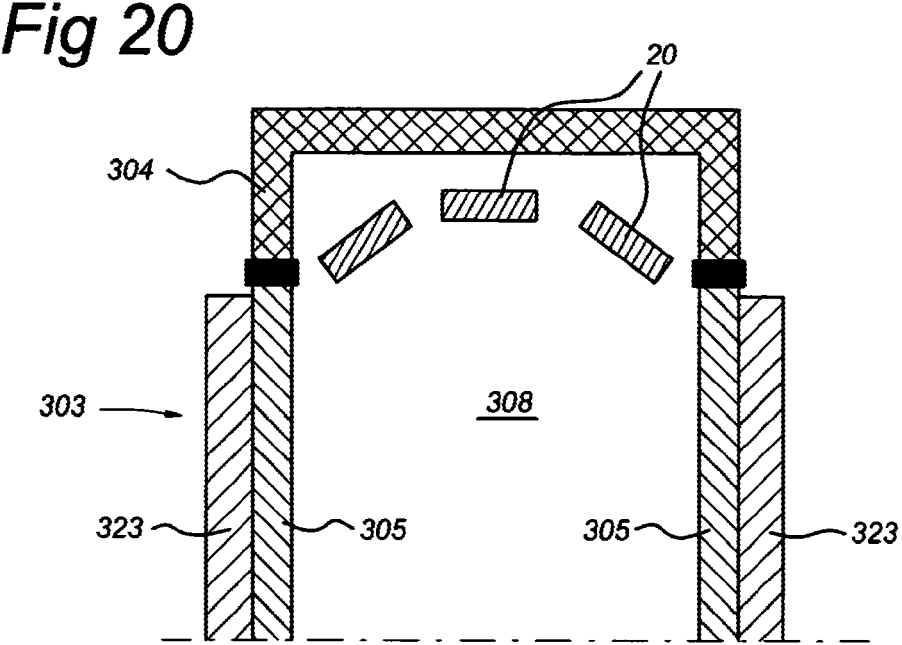
FIG. 20 is a cross-sectional view of an alternative arrangement of a lighting panel.

FIG. 20 is an alternative arrangement of a lighting panel 303. In this arrangement, instead of mounting the LEDs 320 along a plate or strut within the lighting panel 303, the LEDs 320 are mounted in the top of the frame 4 and directed inward to the lighting panel 303. In this embodiment, a surface of the transparent walls 305 of the lighting panel 303, e.g. the outside surface, is covered with a diffusion arrangement, for example a diffusion film or sheet 323. The diffusion arrangement is arranged to diffuse the light emitted by the LEDs 320 so as to distribute the light throughout the bioreactor tank as evenly as possible.

Figure 21:
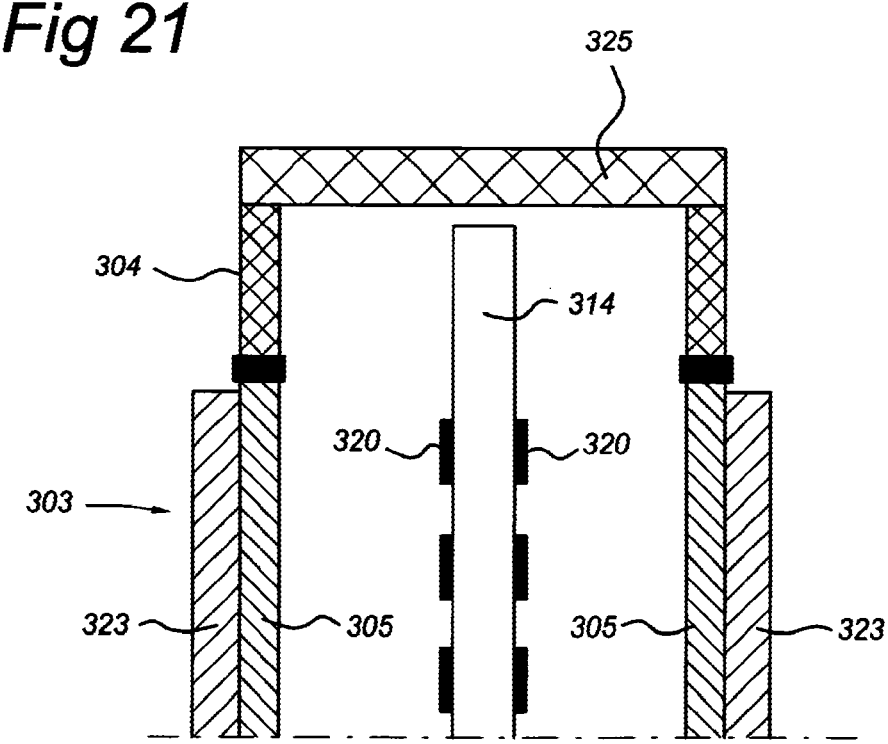
FIG. 21 is a cross-sectional view of another alternative arrangement of a lighting panel with a transparent top portion.

FIG. 21 is yet another alternative arrangement of a lighting panel. In this arrangement, the LEDs 320 are mounted on a mounting strut 314. The frame 304 comprises a top portion or cover structure 325 that is substantially transparent for external light, e.g. sunlight. The transparent top portion 325 may comprise a reflector for (re-)directing sunlight into the housing. In an embodiment, the transparent top portion 325 comprises a filter. Such filter may filter out light with wavelengths that are not considered to be useful for irradiating the photo synthetic culture, for example because the wavelengths will not be absorbed by the photo synthetic culture. The filter may filter out light with wavelengths that are considered to be harmful, for example because these wavelength will limit the growth of the photosynthetic culture. The filter may be replaceable, and may be adapted in view of the type of algae or photosynthetic culture being grown.

The external light that is coupled into the light panel via the cover structure 325 is provided to the aqueous liquid in the tank via the transparent walls 305 of the lighting panel. In an embodiment, for similar reasons as discussed with reference to the embodiment shown in FIG. 20, the (outside) surface of the transparent walls 305 of the lighting panel are provided with a diffusion film or sheet 323.

The embodiment of the lighting panel of FIG. 21 has the advantage that besides light provided by LEDs, the light can be balanced by external light such as sunlight to provide the algae in the bioreactor tank with optimal light conditions. Consequently, it may be possible to obtain the same results with respect to algae growth with less energy consumption by the LEDs 320 as the external light provides an additional light flux. The external light may be collected via light collectors and reflectors and distributed throughout the panel in a controllable way, e.g. by using one or more of lenses, light conductors like fiber optics, and diffusion optics. Some or all of these optical elements may be included in the cover structure 325. In this way, optimal light conditions may be created per algae species.

Figure 22:
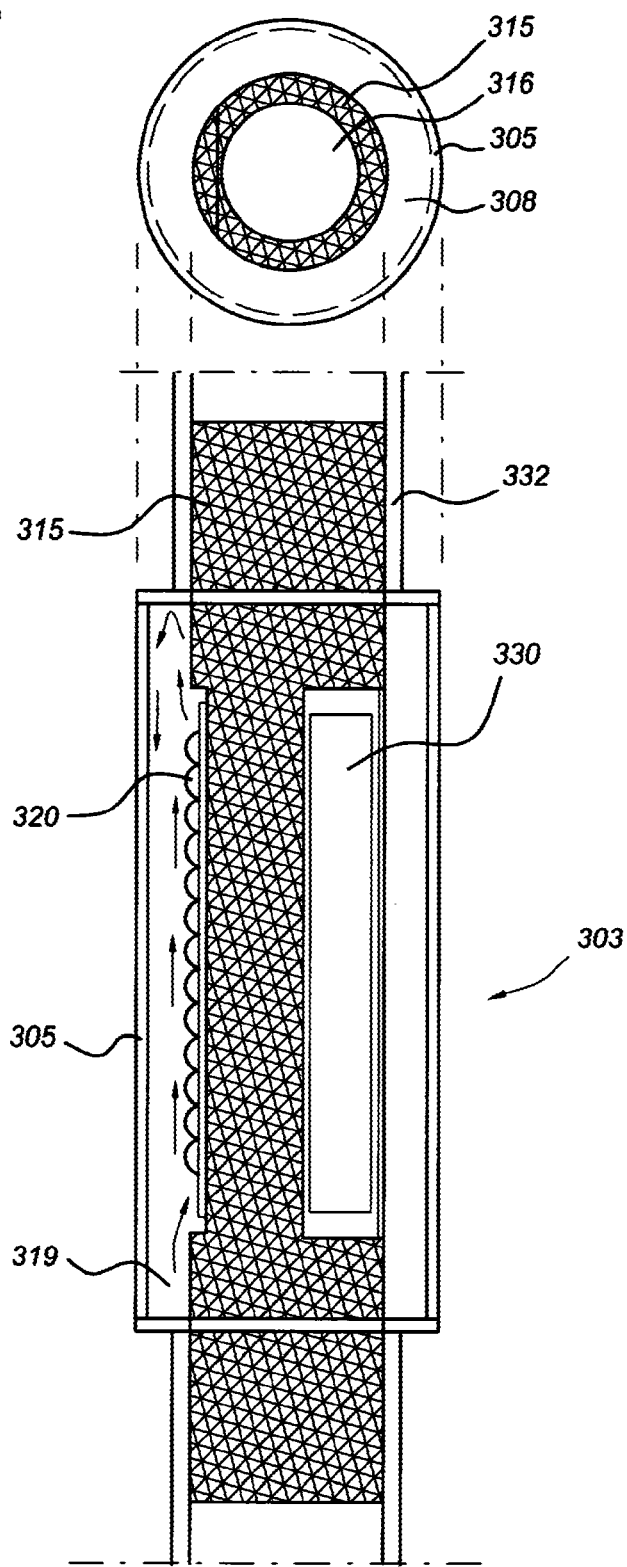
FIG. 22 is a side view and top cross-sectional view of an alternative lighting panel having a tubular housing.

FIG. 22 is a side view and top cross-sectional view of an alternative lighting panel having a tubular housing. The lighting panel includes a tubular mounting structure 315 for supporting light source 330, the tubular mounting structure having an internal channel 316 for a circulation of a cooling liquid for cooling the light source.

The housing includes a transparent wall 305 in a tubular shape, the tubular mounting structure 315 and tubular transparent wall 305 being arranged concentrically. The light source 330 is formed on a planar section formed in the outer surface of the tubular mounting structure 315. The light source includes a strip of LEDs 320 mounted on a ceramic printed circuit board, which is mounted on the planar section. The ceramic carrier may be a metal core PCB to support a large number of LED chips, for example 60 chips. The ceramic carrier with naked bonded LED dies may be glued or eutectic bonded on the flat planar section of the mounting structure 315.

More than one light source 330 may be located at a certain position along the length of the tubular mounting structure. In the embodiment shown in FIG. 22, three light sources 330 are arranged at equal spacing around the circumference of the tubular mounting structure 315. The tubular mounting structure 315 may be formed in long lengths having light sources arranged at several positions along its length. The tubular mounting structure 315 may also be constructed in shorter lengths and joined to other mounting structures using a connecting sleeve 332.

An interior cavity 308 is formed in the gap between the two tubes of the mounting structure 315 and the transparent wall 305, the cavity filled with a cooling liquid 319, e.g. oil with a high refractive index. In one embodiment the amount of oil for this small cavity is minimal. The small quantity of cooling liquid results in minimal circulation of the oil in the cavity 308, which reduces the chance of damage to the bond wire or LED chips and reduces damage or wear and tear caused by any particles of pollution in the cooling liquid.

In another embodiment there is sufficient cooling liquid in the cavity 308 to result in natural convection current in the cooling liquid to enhance the transfer of heat away from the LEDs. The lighting panel is e.g. disposed with its longitudinal axis in a vertical direction to provide a sufficient vertical distance over the length of the light sources 330 to promote the natural convection current within the cooling liquid 319.

The same materials may be used for this embodiment of the lighting panel as the previous embodiment of FIG. 12, for the transparent wall, mounting structure, cooling liquids etc. The materials used for this embodiment e.g. have refractive indices that result in maximizing the light coupling between the LEDs and the water containing the algae, as discussed for the previous embodiments. The same considerations apply for this embodiment and for the previous embodiments. A high refractive index cooling liquid has a positive effect on the light out-coupling from the LEDs to the water/algae, and wetting of the LED chip surface to improve heat transfer. The cooling liquid may also reduce problems of deteriorating encapsulant of the LEDs. A thin film of cooling liquid will also get around the whole tube, ensuring optimal thermal contact between the mounting structure 315 and the transparent wall 305. The cooling liquid may also prevent any electrolyze effects on the light source and connections. The connection wires and electronics to provide a constant driving current to the LEDs can be integrated on the same mounting structure 315 on a flat section of the tube.

Figure 23:
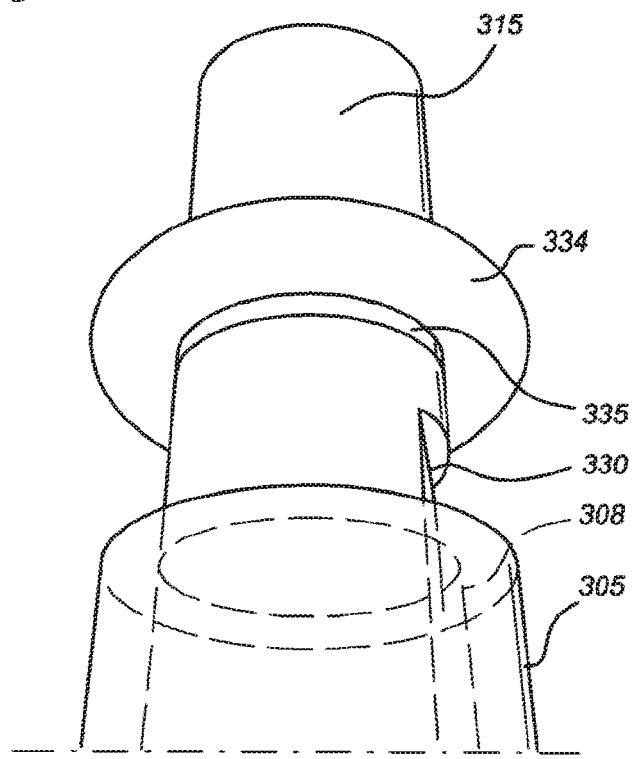
FIG. 23 is a perspective view of the lighting panel of FIG. 22 partially dismantled.

FIG. 23 is a perspective view of the lighting panel of FIG. 22 partially dismantled to show the end cap 334 and sealing ring 335 for sealing off the ends of the cavity 8 formed between the mounting structure 315 and transparent wall 305. The end cap 334 and sealing ring 335 function to separate the cavity 308 from the water of the bioreactor, to keep the cooling liquid from leaking from the cavity and prevent water from entering the cavity. The initial filling of the cavity 308 with the cooling liquid 319 can be done with a thick injection needle through the hole between the transparent wall and the flat planar section of the mounting structure. The transparent wall can then be moved up over the rubber sealing ring 335 and the last part of the oil can be filled through this ring with a thin injection needle.

Figure 24:
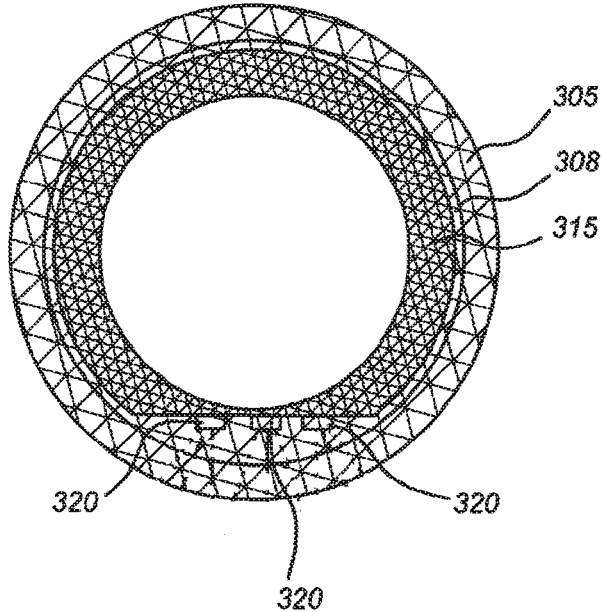
FIG. 24 is a cross-sectional view of the lighting panel of FIG. 22.

FIG. 24 is a cross-sectional view of the lighting panel showing the flat planar portion of the tubular mounting structure 315 where the LEDs 320 of the light sources are located.

Figure 25:
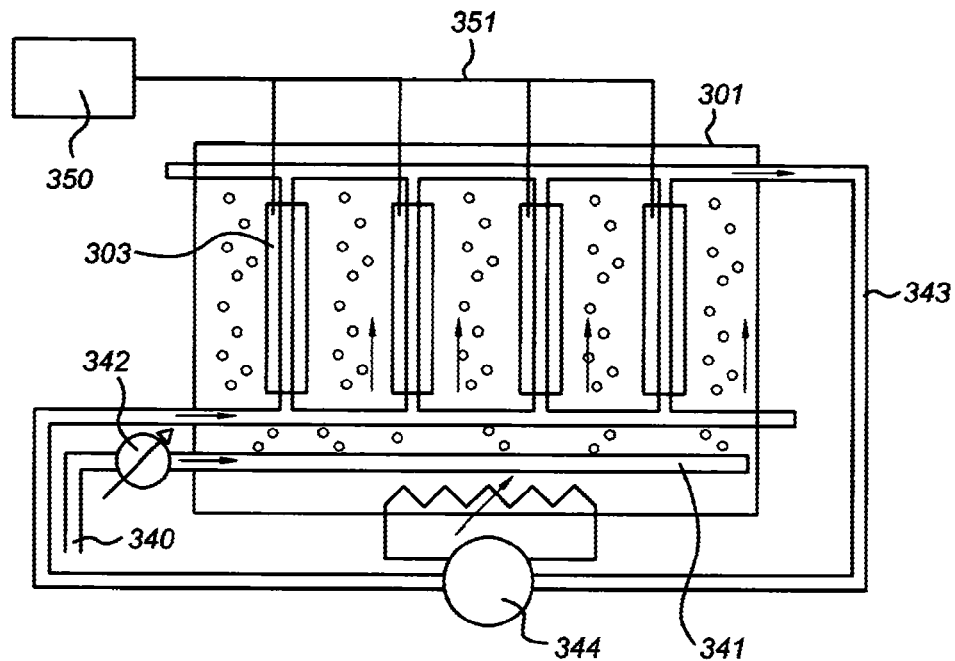
FIG. 25 is simplified schematic diagram of a bioreactor with lighting panels having tubular housings.

FIG. 25 is simplified schematic diagram of a bioreactor with lighting panels 303 comprising a number of LED lamps. The LED lamps may be accommodated in the light panels as described with reference to FIGS. 14 A, 14B or they may be accommodated by tubular housings as described with reference to FIGS. 22-24.

The bioreactor may comprise a $CO_2$ supply system 340 including an applicator 341 to supply carbon dioxide ($CO_2$) to the water containing the algae. In some embodiments the applicator is a $CO_2$ cushion 341 that may extend over the bottom of the bioreactor tank 301. The cushion is provided with a plurality of orifices to dispense and dissolve the $CO_2$ in the water and at the same time create turbulence therein. E.g., the $CO_2$ is added in a form that can be dissolved, e.g. such that the $CO_2$ is absorbed in the liquid to be added to the raceway by the $CO_2$ applicator. The $CO_2$ may be added in such a form that the liquid that is added by the $CO_2$ applicator is always saturated with $CO_2$. The addition of $CO_2$ absorbed via a liquid reduces the occurrence of gaseous bubbles. As such bubbles may cause shear stress in the water which may damage the algae, their presence is e.g. kept to a minimum.

In an embodiment of a bioreactor tank 301 which comprises a $CO_2$ applicator, the LEDs 320 are arranged vertically, for example as shown in FIG. 16 or 22, to provide a consistent light level as $CO_2$ rises through the water.

A cooling fluid is supplied to the LED light source via a separate cooling fluid supply system 343. The cooling fluid corresponds to the second cooling fluid 318 discussed above. The bioreactor further comprises a heater 342 for heating the $CO_2$ before it is supplied to the bioreactor tank in the form of $CO_2$ gas, schematically represented by bubbles in FIG. 25. The bioreactor further comprises a heat exchanger 344 for cooling the cooling fluid. The heat exchanger is arranged to remove heat from the cooling fluid after passage through the lighting panels 303 in the bioreactor, and to supply the heat removed from the cooling fluid to the water containing the algae, and/or a heater for heating the $CO_2$ supplied to the bioreactor, and/or another medium to remove the heat from the system. The reuse of heat from the cooling liquid 318 allows for a bioreactor with a very efficient performance.

It is preferable that the temperature of the LEDs and the temperature of the water containing the algae are under separate control. Although the heat exchanger may reuse heat from the cooling fluid 318 to heat the water or injected $CO_2$, it is preferable that separate control of the cooling fluid temperature and the water temperature is maintained.

The bioreactor also comprises a control system 350 for supplying power to the LED lighting system. Carbon fixation in algae, which part of the photosynthesis process, occurs in the dark. The control system may cycle the LEDs rapidly on and off to increase carbon fixation in the algae and increase the growth rate of the algae, for example switching the LEDs on and off in a cycle of 10 milliseconds on and 10 milliseconds off. The electrical connections 351 to the LEDs are e.g. made at the top of the lighting panels 303 so that the connections are above the water.

In some embodiments of the invention, one or more further arrangements may be provided to prevent continuous exposure of algae to light emitted by the LEDs 20. One arrangement to reach such effect may be to provide a suitable movement of the aqueous liquid within the bioreactor tank. For example, the movement along the raceway or top-down movement as described earlier may qualify as such movements. Additionally or alternatively, a swirling motion may be introduced in the tank, such that at different instants different portions of the algae or photosynthetic culture are exposed.

Instead or in addition to suitable movement of the aqueous liquid comprising the algae, the LEDs 320 may be cycled on and off to accomplish discontinuous exposure. As a result of the discontinuous exposure caused by the suitable movement of the aqueous liquid and/or the on/off-cycle of the LEDs 320, carbon fixation in the algae may increase.

In order to force movement of the aqueous liquid within the bioreactor tank 1, a flow may be induced by means of injecting liquid at suitable positions, hereafter referred to as injection points. The injection points may be located in the bottom of the raceway (bottom flow enhancers) and in the wall of the raceway (side flow enhancers). For the flow enhancers placed under an angle in the wall, the angle is such that an upward flow is achieved.

In an embodiment, the liquid flow is added at an elevated pressure of 1-15 bars (per surface). In this way, the pressure difference between the main flow and the locally introduced extra liquid flow may affect the motion of the algae. The additional liquid flow may be adjustable to the viscosity of the aqueous liquid with algae If required, a pumping system can be used to deliver the additional liquid flow with a specific flow rate and with a specific density and viscosity.

In an embodiment, the pumping system is a disc pump. A disc pump is a pump comprising one or more discs to perform the pumping action. Due to the use of discs, damage to algae is avoided.

Figure 26A:
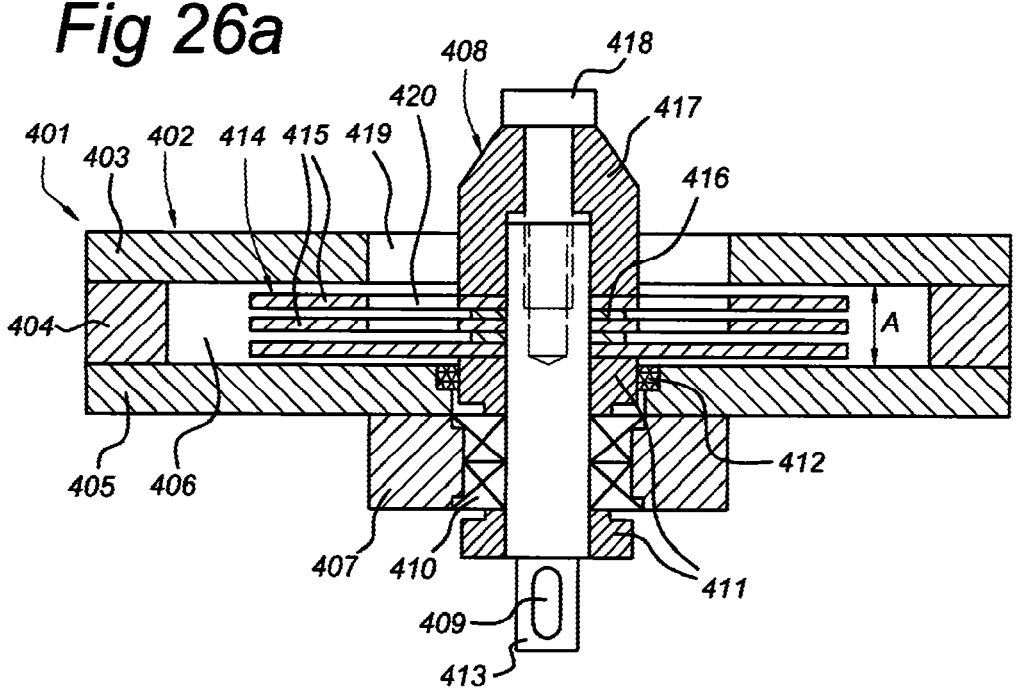
FIG. 26A is a cross-sectional view of a disc pump for a bioreactor.
Figure 26B:
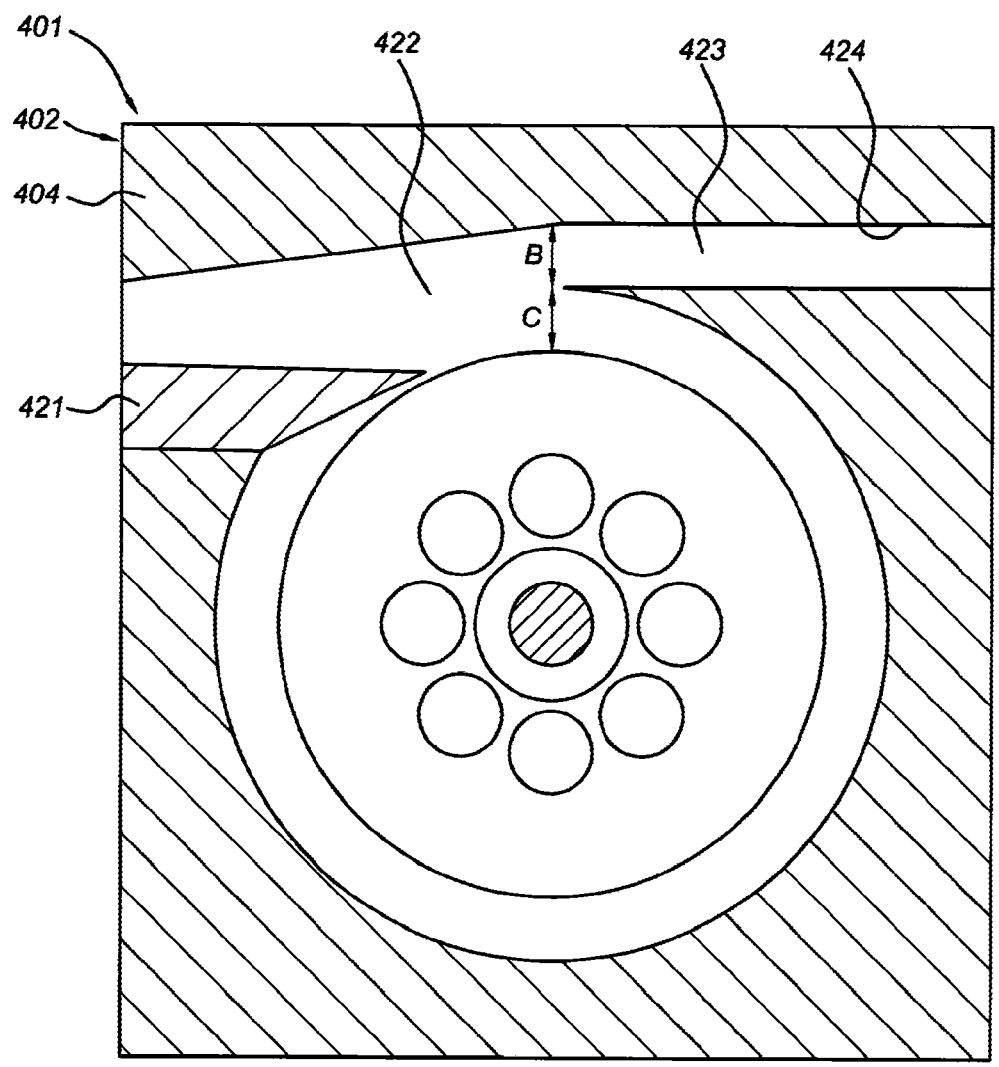
FIG. 26B is another cross-sectional view of the disc pump of FIG. 26 A.

FIG. 26A shows a cross-sectional view of an embodiment of a disc pump. FIG. 26B shows a longitudinal sectional view of the same pump. The pump 401 comprises a housing 402 comprising a front plate 403, an intermediate plate 404 and a rear plate 405. The plates made be made of steel or of a plastic. The plates may be pressed together by bolts or the like (not shown). The intermediate plate 404 is provided with a circularly cylindrical recess, which, together with the front plate 403 and the rear plate 405, defines a chamber 406. The rear plate 405 comprises a bearing housing 407, in which a composite shaft 408 is rotatably accommodated by means of two bearings 410, e. g. double-seal ball bearings. The bearings 410 are clamped between two internally threaded rings 411, the inner ring 411 of which is sealed by a ring-shaped gasket 412. The shaft 408 is provided with a keyway 409, by means of which the shaft 408 can be connected to a drive unit, such as an electric motor.

Mounted on the central portion 413 of the shaft 408 is a rotor 414 which comprises a number of flat, round discs 415. The discs may be made of steel, stainless steel or a plastic, such as PVC or polycarbonate. The discs 415 are separated from each other by means of ring-shaped spacers 416. Additionally, the discs are pressed against the inner ring 411 by means of a clamping piece 417. In its turn, the clamping piece is mounted over the central portion 413 of the shaft 108 by means of a bolt 418. The discs 415 and the chamber 406 together form a so-called Tesla pump. Details of the design and operation of Tesla pumps are provided in U.S. Pat. No. 1,061,142 which is hereby incorporated by reference in its entirety. The larger the surface area and/or the number of discs, the larger the delivery and the propelling force of said pump will be.

The front plate 403 comprises a circular opening which fits over the clamping piece 117, forming an annular, axial inlet 419 therewith. As FIG. 26 A shows, the discs 415 may be provided with a number of holes 420. Furthermore, a wedge-shaped insert 421 is mounted in the housing 402, which insert forms an outlet channel 422 together with the front plate 403, the intermediate plate 404 and the rear plate 405.

The pump is provided with a substantially tangential bypass channel 423, a first end of which opens into the outlet channel 422 of the pump 401, and a second end of which forms an inlet 424. The bypass channel 423 is formed in the intermediate plate 404 and has the same width A as the chamber 406. In order to ensure that the flow from the chamber is powerful enough to generate a significant flow through the bypass channel 423, the height B of the channel 423 at the outlet channel 422 is equal to or smaller than the distance C between an imaginary line transversely to the periphery of the rotor 414 and the internal wall of the chamber 406, likewise at the outlet channel 422.

The bypass channel 423 may be provided with an inlet for supplying carbon dioxide gas to the aqueous liquid. By supplying carbon dioxide gas in this manner, the size of carbon dioxide bubbles very small. Such small $CO_2$-bubbles cause minimal damage to the photosynthetic culture.

It will also be obvious after the above description and drawings are included to illustrate some embodiments of the invention, and not to limit the scope of protection. Starting from this disclosure, many more embodiments will be evident to a skilled person which are within the scope of protection and the essence of this invention and which are obvious combinations of prior art techniques and the disclosure of this patent.

The term "substantially" herein, such as in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements.

The mere fact that certain measures are recited in mutually different dependent claims does not indicate that a combination of these measures cannot be used to advantage.

The invention claimed is:

1. A photo bioreactor system for growing a photosynthetic culture in an aqueous liquid, the photo bioreactor system comprising:
   a. a vessel arranged to contain the aqueous liquid; and
   b. a lighting system arranged to irradiate the photosynthetic culture below the surface of the aqueous liquid, wherein the lighting system comprises coupled lighting panels that form canal sections in the vessel, the lighting panels being arranged to be at least partially submerged in the aqueous liquid,
   wherein each lighting panel comprises transparent sidewalls forming a compartment, the compartment containing a light source for lighting the photosynthetic culture, the lighting panel being free of an air gap between the sidewalls and the light source; and
   wherein the photo bioreactor system further comprises a harvester system having a scoop construction comprising a scoop, arranged to scoop at least part of the photosynthetic culture from the aqueous liquid, and a collector system, arranged to collect at least part of the scooped photosynthetic culture, wherein the scoop comprises a sieve, arranged to scoop a predetermined fraction of the photosynthetic culture.

2. The photo bioreactor system according to claim 1, wherein the photo bioreactor system comprises a controlled environment, a closed environment, or a controlled and closed environment.

3. The photo bioreactor system according to claim 1, wherein the lighting system comprises a light source arranged to irradiate the photosynthetic culture below the surface of the aqueous liquid.

4. The photo bioreactor system according to claim 3, wherein the lighting system comprises a reflector arranged to reflect light of the light sources below the surface of the aqueous liquid into the aqueous liquid.

5. The photo bioreactor system according to claim 4, wherein the reflector is rotatable connected with respect to the lighting panel.

6. The photo bioreactor system according to claim 1, wherein the scoop comprises meshes, and wherein the meshes have a mesh size in the range of about 0.5-35 µm.

7. The photo bioreactor system according to claim 1, wherein the scoop construction comprises a paddle wheel construction comprising at least one paddle, wherein the paddle comprises the scoop, and wherein the scoop construction is arranged to move the scoop between a position above the surface of the aqueous liquid and a position below the aqueous liquid.

8. The photo bioreactor system according to claim 7, wherein the scoop construction is arranged to rotate the scoop.

9. The photo bioreactor system according to claim 7, wherein the collector system is arranged to receive the scooped photosynthetic culture dropping from the scoop.

10. The photo bioreactor system according to claim 1, wherein the harvester system further comprises a harvester transporter, arranged to allow the scoop construction to scoop at different positions in the aqueous liquid.

11. The photo bioreactor system according to claim 10, wherein the transporter comprises a rail.

12. The photo bioreactor system according to claim 1, wherein the harvesting system comprises a cleaning unit arranged to clean the lighting system.

13. The photo bioreactor system according to claim 1, wherein the collector system further comprises a product transporter, arranged to transport the collected scooped photosynthetic culture to a storage unit.

14. The photo bioreactor system according to claim 1, further comprising a dryer, arranged to dry the collected scooped photosynthetic culture.

15. The photo bioreactor system according to claim 1, wherein the harvester system is further arranged to create turbulence in the aqueous liquid.

16. The photo bioreactor system according to claim 1, further comprising a $CO_2$-applicator to supply $CO_2$ to the aqueous liquid.

17. The photo bioreactor system according to claim 1, further comprising a flow enhancement system comprising a flow enhancement body provided with a profile for engaging the aqueous liquid for increasing turbulence in the aqueous liquid.

18. The photo bioreactor system according to claim 17, wherein the flow enhancement system comprises a funnel system comprising an inlet for liquid and an inlet for a nutrient, and an outlet for the liquid and the nutrient.

19. The photo bioreactor system according to claim 17, wherein the flow enhancement system comprising an obstacle, arranged in the vessel.

20. The photo bioreactor system according to claim 19, wherein the obstacle is arranged in line with the outlet of the funnel system.

21. The photo bioreactor system according to claim 1, wherein the photo bioreactor system comprises a greenhouse.

22. The photo bioreactor system according to claim 1, wherein the lighting panel is waterproof, so that an interior cavity is formed in the lighting panel, separated from the aqueous liquid in the bioreactor when the lighting panel is placed into said aqueous liquid.

23. The photo bioreactor system according to claim 22, wherein the interior cavity is free of an air gap between the sidewalls and the light sources.

24. The photo bioreactor system according to claim 22, wherein the interior cavity is free of the aqueous liquid.

25. The photo bioreactor system according to claim 22, wherein the interior cavity houses a liquid.

26. The photo bioreactor system according to claim 25, wherein said liquid housed in the interior cavity is a cooling liquid.

27. The photo bioreactor system according to claim 26, wherein said cooling liquid is circulated in the interior cavity.

28. The photo bioreactor system according to claim 1, wherein said coupled lighting panels are arranged end-to-end to form at least a section of a wall that defines canal sections in the vessel.

29. The photo bioreactor system according to claim 28, wherein the panels are arranged end-to-end with the interface between the panels forming a smooth surface of the wall to avoid impeding the flow of the liquid in the vessel along the length of the wall formed by the panels.

30. The photo bioreactor system according to claim 29, wherein the panels comprise flanges as coupling means to couple the lighting panels together with the interface between the panels forming a smooth surface.

31. The photo bioreactor system according to claim 29, wherein the vessel is a pond and the canal sections are raceways for the flow of the liquid.

* * * * *